(12) United States Patent
Matusik

(10) Patent No.: US 10,314,988 B2
(45) Date of Patent: Jun. 11, 2019

(54) GAS FLOW INDICATOR

(71) Applicant: VPAS GROUP PTY LTD, Malvern East (AU)

(72) Inventor: Matthew Matusik, Malvern East (AU)

(73) Assignee: VPAS Group Pty Ltd, Malvern East (AU)

(*) Notice: Subject to any disclaimer, the term of this patent is extended or adjusted under 35 U.S.C. 154(b) by 514 days.

(21) Appl. No.: 14/421,039

(22) PCT Filed: Aug. 12, 2013

(86) PCT No.: PCT/AU2013/000884
§ 371 (c)(1),
(2) Date: Feb. 11, 2015

(87) PCT Pub. No.: WO2014/026221
PCT Pub. Date: Feb. 20, 2014

(65) Prior Publication Data
US 2015/0196723 A1 Jul. 16, 2015

Related U.S. Application Data

(60) Provisional application No. 61/682,265, filed on Aug. 12, 2012, provisional application No. 61/763,492, filed on Feb. 12, 2013.

(51) Int. Cl.
*A61M 16/08* (2006.01)
*A61M 16/20* (2006.01)
(Continued)

(52) U.S. Cl.
CPC ........ *A61M 16/0003* (2014.02); *A61M 16/06* (2013.01); *A61M 16/08* (2013.01);
(Continued)

(58) Field of Classification Search
CPC .. A61M 16/0003; A61M 16/06; A61M 16/08; A61M 16/20; A61M 16/0816; A61M 2016/003; A61M 2205/582; G01F 15/06
See application file for complete search history.

(56) References Cited

U.S. PATENT DOCUMENTS 828,108 A * 8/1906 Graham ................. F16N 29/00
116/273
2,389,282 A 11/1945 Stegeman
(Continued)

FOREIGN PATENT DOCUMENTS

DE 176885 8/1964
EP 1 832 854 A1 9/2007
(Continued)

OTHER PUBLICATIONS

International Patent Application No. PCT/AU2013/000884, International Search Report, pp. 1-4, issued by Australian Patent Office.
(Continued)

*Primary Examiner* — Timothy A Stanis
(74) *Attorney, Agent, or Firm* — IP Attorneys Group, LLC

(57) ABSTRACT

A gas flow indicator apparatus (10) comprising: a gas flow chamber including at least one transparent portion (30) and at least one opaque portion (36); at least one inlet port (34); at least one outlet port (32); and, at least one gas flow signal means (18) movably disposed within the gas flow chamber. The gas flow indicator apparatus (10) being configured such that when no gas flow is present and/or when a predetermined gas flow rate has not been achieved, the signal means (18) is disposed substantially within one of the transparent portion (30) or the opaque portion (36), and wherein when gas flow is present and/or the predetermined gas flow rate has been achieved, the signal means (18) is moved to be disposed substantially within the other of the transparent
(Continued)

portion (30) or the opaque portion (36). Gas delivery devices (12), systems (12) and/or conduits (16) incorporating the gas flow indicator apparatus (10) are also provided in accordance with the invention.

14 Claims, 12 Drawing Sheets

(51) Int. Cl.
*A61M 16/00* (2006.01)
*A61M 16/06* (2006.01)
*A61M 16/12* (2006.01)

(52) U.S. Cl.
CPC ........ *A61M 16/0816* (2013.01); *A61M 16/20* (2013.01); *A61M 16/0875* (2013.01); *A61M 16/127* (2014.02); *A61M 2016/003* (2013.01); *A61M 2202/0208* (2013.01); *A61M 2205/3334* (2013.01); *A61M 2205/583* (2013.01)

(56) References Cited

U.S. PATENT DOCUMENTS

| | | | |
|---|---|---|---|
| 2,662,502 A * | 12/1953 | Turner | A62C 13/003 116/273 |
| 2,843,121 A | 7/1958 | Hudson | |
| 3,119,369 A | 1/1964 | Harland et al. | |
| 3,256,876 A | 6/1966 | Elam | |
| 3,408,865 A | 11/1968 | Chenault | |
| 3,650,599 A | 3/1972 | Pedersen | |
| 3,890,967 A | 6/1975 | Elam et al. | |
| 4,064,751 A * | 12/1977 | Deisenroth | G01F 1/26 73/861.53 |
| 4,098,271 A | 7/1978 | Maddock | |
| D256,000 S | 7/1980 | Molijn | |
| D266,316 S | 9/1982 | Du Vall | |
| 4,745,877 A | 5/1988 | Chang | |
| 4,763,114 A | 8/1988 | Eidsmore | |
| 4,938,078 A | 7/1990 | Kobold | |
| 4,945,918 A | 8/1990 | Abernathy | |
| 5,038,773 A | 8/1991 | Norlien et al. | |
| 5,337,617 A * | 8/1994 | Dimeff | G01F 1/24 73/861.54 |
| 5,343,859 A | 9/1994 | Kikut | |
| 5,606,131 A | 2/1997 | Pope | |
| 5,845,597 A * | 12/1998 | Karpal | G01L 7/166 116/268 |
| 5,857,460 A | 1/1999 | Popitz | |
| 5,911,219 A | 6/1999 | Aylsworth et al. | |
| 6,338,279 B1 | 1/2002 | Tsataros | |
| 6,386,196 B1 | 5/2002 | Culton | |
| 7,004,168 B2 | 2/2006 | Mace et al. | |
| 7,013,726 B1 * | 3/2006 | Drummond | A61M 16/20 417/413.2 |
| 7,040,319 B1 | 5/2006 | Kelly et al. | |
| 7,055,520 B2 | 6/2006 | Swisa | |
| 7,159,533 B1 | 1/2007 | Redd et al. | |
| D551,999 S | 10/2007 | Makkonen et al. | |
| 7,730,847 B1 | 6/2010 | Red et al. | |
| 7,891,311 B2 | 2/2011 | Logan et al. | |
| D657,399 S | 4/2012 | Memoto | |
| 2005/0205098 A1* | 9/2005 | Lampotang | A61M 16/12 128/207.18 |
| 2006/0070458 A1 | 4/2006 | Jones et al. | |
| 2006/0130838 A1 | 6/2006 | Lee et al. | |
| 2006/0266133 A1 | 11/2006 | Kim et al. | |
| 2007/0221223 A1* | 9/2007 | McDermott | A61M 16/08 128/204.22 |
| 2009/0114225 A1 | 5/2009 | Tappehorn et al. | |
| 2009/0145349 A1 | 6/2009 | Herbert | |
| 2009/0165801 A1 | 7/2009 | Ostrowski | |
| 2009/0301474 A1* | 12/2009 | Korneff | A61M 16/1045 128/201.13 |
| 2010/0282253 A1 | 11/2010 | Newman, Jr. | |
| 2012/0048274 A1 | 3/2012 | Bayron | |
| 2012/0055471 A1 | 3/2012 | Hadas et al. | |
| 2012/0298109 A1 | 11/2012 | Phifer et al. | |
| 2012/0325215 A1 | 12/2012 | Levenick et al. | |
| 2015/0196723 A1 | 7/2015 | Matusik | |

FOREIGN PATENT DOCUMENTS

| | | |
|---|---|---|
| GB | 1396759 | 6/1975 |
| GB | 2073893 | 10/1981 |
| WO | 2006/106632 A1 | 10/2006 |

OTHER PUBLICATIONS

International Patent Application No. PCT/AU2013/000884, Written Opinion of the International Searching Authority, pp. 1-5, issued by Australian Patent Office.

Extended European Search Report for EP13829326.1; issued by European Patent Office dated Feb. 22, 2016; pp. 1-7.

International Preliminary Report on Patentability for I.A. PCT/AU2013/000884; issued by Australian Patent Office dated Feb. 17, 2015; pp. 1-6.

First Examination Report for NZ705892; issued by New Zealand Patent Office dated Jun. 13, 2016; pp. 1-2.

First Examination Report for AU2013302298; issued by Australian Patent Office dated Nov. 23, 2016.

New Zealand Patent Application No. 705892, Second Examination Report, pp. 1-2, issued by New Zealand Patent Office dated Jan. 5, 2017.

New Zealand Patent Application No. 705892, Third Examination Report, pp. 1-2, issued by New Zealand Patent Office dated Feb. 10, 2017.

New Zealand Patent Application No. 705892, Notice of Acceptance, p. 1, issued by New Zealand Patent Office dated Jun. 13, 2017.

New Zealand Patent No. 705892, Certificate of Grant, Letters Patent, p. 1, issued by New Zealand Patent Office dated Oct. 3, 2017.

New Zealand Patent No. 705892, Granted Patent Specification (B2 Specification), pp. 1 to 54, published by New Zealand Patent Office dated Oct. 27, 2017.

Australian Patent Application No. 2013302298, Notice of Acceptance, pp. 1-4, issued by the Australian Patent Office dated Nov. 28, 2017.

Australian Patent No. 2013302298, Standard Patent Certificate, p. 1, issued by the Australian Patent Office dated Mar. 22, 2018.

Australian Patent No. 2013302298, Granted Patent Specification (B2 Specification), pp. 1-56, published by the Australian Patent Office dated Dec. 7, 2017.

European Patent Application No. 13 829 326.1, Communication under Rule 71(3) EPC (Intention to Grant), pp. 1-5, issued by the European Patent Office dated May 16, 2018.

Australian (Divisional) Patent Application No. 2017261637, First Examination Report, pp. 1-4, issued by the Australian Patent Office dated Apr. 21, 2018.

New Zealand (Divisional) Patent Application No. 732790, First Examination Report, pp. 1-4, issued by New Zealand Patent Office dated Feb. 12, 2018.

New Zealand (Divisional) Patent Application No. 732790, Second Examination Report, pp. 1-4, issued by New Zealand Patent Office dated May 9, 2018.

EPO machine translation of DE 1176885 (Published Aug. 27, 1964, to Dipl-Ing Hubert Jung), translated Jul. 25, 2018.

New Zealand (Divisional) Patent Application No. 732790, Third Examination Report, pp. 1-3, issued by New Zealand Patent Office dated Sep. 5, 2018.

European Patent Application No. 13 829 326.1, Communication pursuant to Article 94(3) EPC (Office Action), pp. 1-4, issued by the European Patent Office dated Oct. 4, 2018.

\* cited by examiner

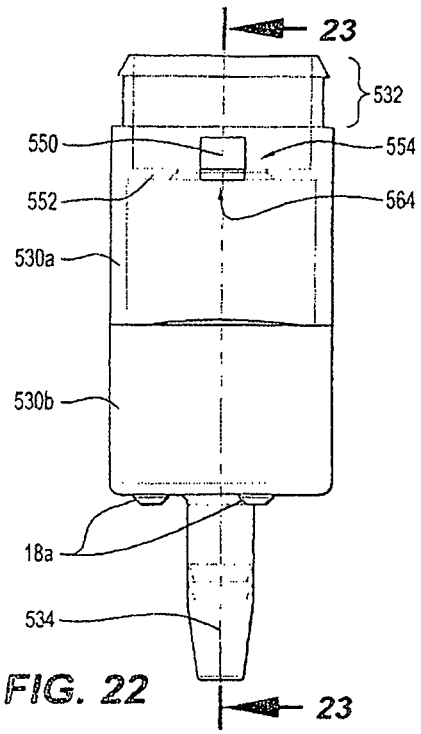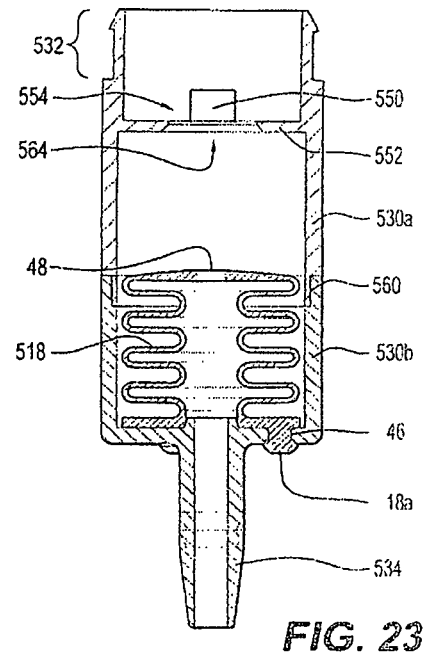
FIG. 22  FIG. 23
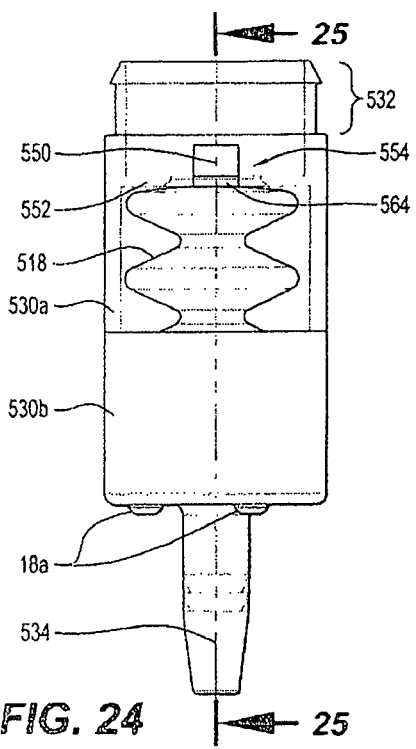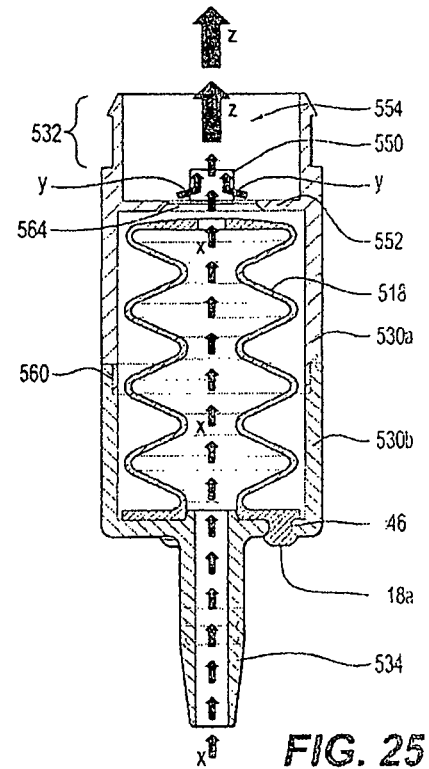
FIG. 24  FIG. 25

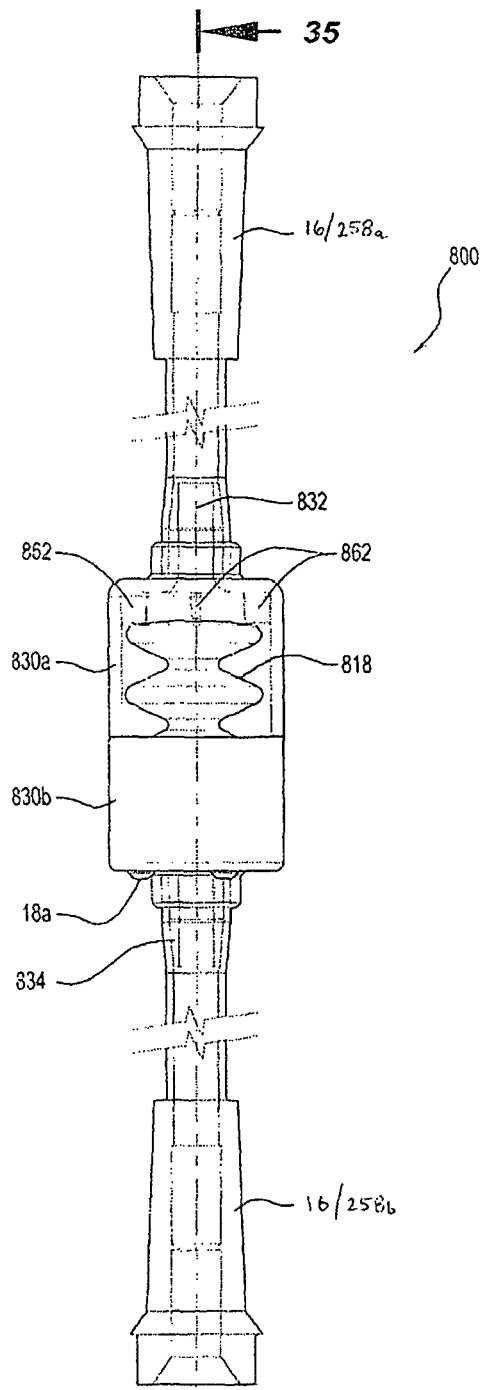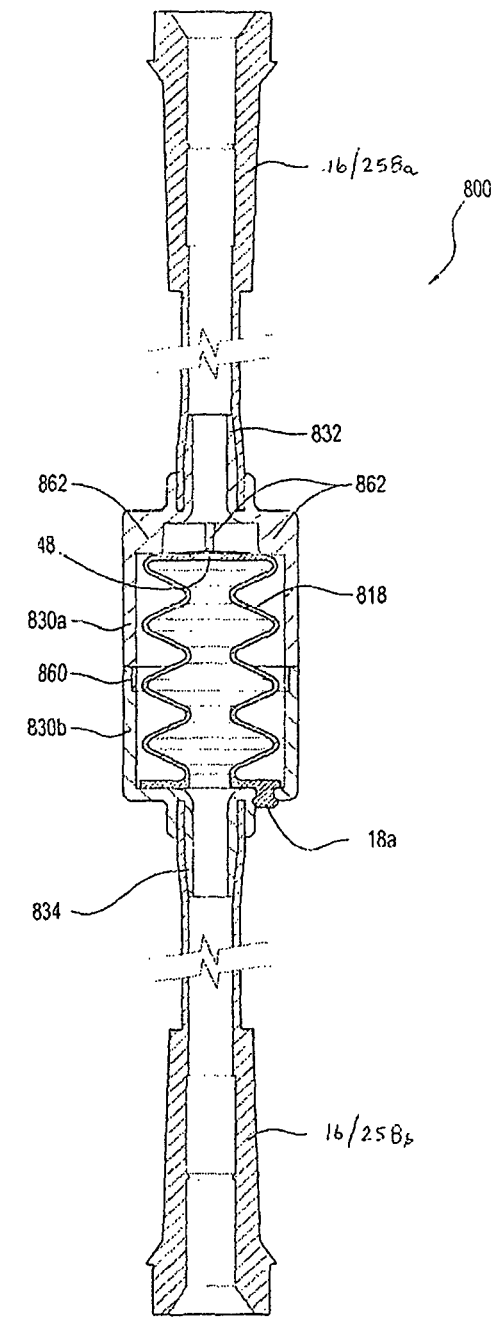
FIG. 34
FIG. 35

GAS FLOW INDICATOR

CROSS-REFERENCE

This application claims priority to U.S. Provisional Patent Application Ser. No. 61/682,265, filed on Aug. 12, 2012, and U.S. Provisional Patent Application Ser. No. 61/763,492, filed on Feb. 12, 2013, the entire contents of each of which are incorporated herein by reference.

TECHNICAL FIELD

The present invention relates generally to gas monitoring apparatus. More particularly, the present invention relates to gas flow indicator apparatus for gas delivery devices, systems, and/or gas supply conduits.

It will be convenient to hereinafter describe the invention in relation to gas flow indicator apparatus for medical devices, systems and/or conduits that deliver breathing gas(es) to an individual's airway, however, it should be appreciated that the present invention is not limited to that use only. For example, an alternative use for gas flow indicator apparatus made in accordance with the present invention could include breathing gas delivery devices, systems, etc., for use in the aviation industry. Moreover, gas flow indicator apparatus made in accordance with the present invention could also be used for other, non-breathing gas applications, gas delivery devices, gas delivery systems, or gas supply systems, without departing from the spirit and scope of the invention as hereinafter described. Accordingly, the present invention should not be construed as limited to any one or more of the specific examples provided herein.

BACKGROUND ART

Any discussion of documents, devices, acts or knowledge in this specification is included to explain the context of the invention. It should not be taken as an admission that any of the material forms a part of the prior art base or the common general knowledge in the relevant art in the United States of America, Australia, or elsewhere, on or before the priority date of the disclosure herein.

Unless stated otherwise, throughout the ensuing description, the expression "gas(es)" refers to any suitable gas, or mixture of gases and/or gaseous elements or agents, that can be monitored using gas flow indicator apparatus of the present invention. In the context of medical or other respiratory applications of gas flow indicator apparatus of the present invention, "gas" refers to any suitable breathing gas(es) which will generally be oxygen, or a mixture of oxygen and one or more inert gases and/or pharmacological agents, and/or air which of course is a combination of oxygen and other gases/elements. Similarly, the expressions "gas delivery device(s)" or "gas delivery system(s)" refer to any suitable device(s), system(s), and/or conduit(s) for supplying gas(es) to, or at, a desired location. In the context of medical or other respiratory applications of the gas flow indicator apparatus of the present invention, "gas delivery device(s)" or "gas delivery system(s)" refer to any suitable breathing apparatus, system and/or supply conduit(s), etc., for introducing or supplying gas(es) into/to an individual's airway. For example, for individuals breathing spontaneously suitable apparatus, systems, etc., may include, but are not limited to: face masks; mouth pieces; nasal cannulas; and/or, gas supply conduit(s). Whereas for non-spontaneous breathing applications suitable apparatus, systems, etc., may include, but are not limited to; manual resuscitator devices, such as bag valve masks; endotracheal tubes; and/or, gas supply conduit(s). A skilled person will appreciate many such devices, systems, conduits, etc., alternatives, and/or variations thereof, and hence the present invention should be construed as including within its scope any suitable means of supplying gas to an individual's airway. Finally, the definitions of the expressions hereinbefore described are only provided for assistance in understanding the nature of the invention, and more particularly, the preferred embodiments of the invention as hereinafter described. Such definitions, where provided, are merely examples of what the expressions refer to, and hence, are not intended to limit the scope of the invention in any way.

Supplemental gas is widely used in the medical field. For example, supplemental oxygen is used to assist or maintain safe normal blood levels of oxygen within a patient. The duration of supply of supplemental oxygen varies depending on the condition of the patient and/or the particular circumstance necessitating the administration of the supplemental oxygen supply. Common scenarios include patients having a cardiorespiratory disease or dysfunction and/or surgical/anaesthetic interventions that mandate supplementation of atmospheric air with higher concentrations of inspired oxygen in order to achieve normal oxygen tensions in the patient's blood. Failure to deliver this supplemental oxygen can lead to risk of reduced arterial oxygen tension which, if uncorrected, contributes directly to increased morbidity and mortality.

Failure of supplemental gas delivery is an acknowledged and feared system risk in the hospital environment. To safeguard from this, more often than not there are multilevel complex alarms and flow sensors within the hospital's in-built gas piping circuitry, and/or at gas supply outlets provided throughout hospital facilities. In addition, anaesthetic machines, intensive care ventilators, or the likes, have mandatory flow sensors engineered into their design to detect and alert of gas supply failure.

Although most hospital's gas supply systems, from source to supply outlet, are generally monitored, as are complex anaesthetic machines and/or ventilators, the most commonly used, and often most simple, gas delivery devices, systems and/or conduits, are not provided with any gas flow indicator apparatus, or at least any effective or useful gas flow indicator apparatus. Hence, use of such gas delivery devices, systems, etc., can lead to supplementary gas delivery or supply failure going unnoticed. This risk is magnified in situations involving gas supply from portable gas tanks or cylinders.

One of the most commonly used gas delivery devices for spontaneously breathing patients is the gas delivery mask, or oxygen mask. Sometimes called the "Hudson Mask", with reference to the early mask innovations of the Hudson Company, most such masks are made of a clear plastics material and include a body, which is either resilient or rigid, that is sized to seat over the nose and mouth of a patient. With conventional mask designs, gas is introduced through a gas inlet, and expiratory gases are vented from either around the side of the mask and/or through appropriately placed ventilation apertures. Gas is supplied to the gas inlet from a gas supply source, commonly by way of a length of clear plastic conduit. The gas supply source may be an in-built hospital supply source, or a gas tank or cylinder.

Oxygen masks are designed to increase a patient's inspired fraction of oxygen from about 21% to about 40%. The oxygen flow rate required to achieve this is about 6 liters per minute ("6 L/min"). When oxygen flow into the mask fails, not only is the desired ~40% inspired oxygen concentration not achieved, but of greater concern, the patient re-breathes their expired gases which cannot be satisfactorily replenished by entrainment of air around the side of the mask, ultimately leading to the inspiration of a hypoxic gas mixture (oxygen concentration of less than 21%). As oxygen masks are not presently provided with any visual indicator confirming the presence of oxygen flow into the mask, or in the oxygen supply conduit proximate the mask, complete lack of oxygen flow or insufficient flow (i.e. less than 6 L/min) is not inherently obvious to a medical practitioner, carer, or to the patient themselves, such as in circumstances where individual's administer their own supplemental oxygen supply. A visual inspection of the oxygen delivery system (e.g. conduit and mask), distal to the oxygen supply outlet or source, will not generally indicate whether oxygen is or isn't flowing. For this reason, often medical practitioners, etc., find themselves having to use their ears as a means of identifying oxygen flow. Although putting ones ear at or near a mask, etc., may sometimes identify that gas is flowing, the medical practitioner still has no way of knowing whether the desired flow rate of oxygen (i.e. about 6 L/min) is present in or at the mask.

For non-spontaneously breathing patients, one of the most commonly used manual resuscitator gas delivery devices is the bag valve mask or "BVM". Sometimes called the "AMBU" bag or mask, with reference to the proprietary name appointed by the inventors' of the original BVM, such devices consist of a flexible air chamber (the "bag") attached to a face mask or endotracheal tube via a shutter valve. When the mask is properly applied to a patient (or endotracheal tube is correctly inserted into the patients trachea) and the "bag" is squeezed, the device forces air into the patient's lungs. When the bag is released, it self-inflates from its supply end, drawing in either ambient air or oxygen supplied by an oxygen supply source, while also allowing the patient's lungs to deflate to the ambient environment (and not the "bag") by way of a one-way expired air valve. The BVM generally includes two inlet ports for drawing in ambient air or oxygen. When available, oxygen is supplied to one of the inlet ports from a gas supply source, commonly by way of a length of clear plastic conduit. The gas supply source may be an in-built hospital supply source, or a gas tank or cylinder. The other inlet port can then be used to draw in ambient air, or to connect a reservoir for catching unused oxygen between compressions of the "bag". In case oxygen flow is not sufficient to fill the "bag", the reservoir generally includes a one-way valve for drawing in ambient air to ensure that the BVM continues to supply at least ambient air to the patient.

BVM's are designed to deliver up to 100% inspired oxygen to a patient. With a loss of supplemental oxygen supply into the "bag", the BVM will continue to entrain ambient air (with an oxygen concentration of about 21%) with which to ventilate the patient. However, patient's requiring the use of such manual resuscitator devices often have severely compromised respiratory function, which means that they require much higher inspired oxygen concentrations than that of ambient air. Therefore any loss of supplemental oxygen supply can have catastrophic sequelae if undiagnosed. Like in the case of the common oxygen mask described above, loss of oxygen supply to a BVM can be, and often is, missed as there is presently no visual flow indicator provided at or proximate the BVM confirming supplemental oxygen inflow. Again, although the presence of a sound may indicate that gas is flowing, the medical practitioner still has no way of knowing whether the required flow rate of oxygen is present at the BVM.

Often gas tanks or cylinders are used to supply oxygen to masks or BVM's, most commonly in emergency, perioperative, critical care or transport scenarios. While some cylinders do have ball-type flow indicators at their supply outlets, such cylinders are often placed in visually obscured positions (e.g. under a patient's bed or transportation trolley), or placed side-ways rendering the ball-type flow indicators inaccurate. Additionally, most cylinders do not have alarms in the event of cylinder oxygen supply running empty during use to indicate oxygen supply failure. Even more concerning is that newer designs of oxygen cylinders commonly no longer have ball-type or any flow indicator incorporated into their design. Hence, failure of supplemental gas supply to gas delivery devices or systems is a real and likely problem.

It would be desirable to overcome or alleviate one or more of the aforesaid problems associated with the use of known gas delivery devices, systems, and/or conduits, more particularly, breathing gas delivery devices, systems, and/or conduits, or at least to provide a useful alternative.

DISCLOSURE OF THE INVENTION

According to a first aspect, the present invention provides a gas flow indicator apparatus comprising: a gas flow chamber including at least one transparent portion and at least one opaque portion; at least one inlet port; at least one outlet port; and, at least one gas flow signal means movably disposed within the gas flow chamber, wherein when no gas flow is present and/or a predetermined gas flow rate has not been achieved, the at least one gas flow signal means, or at least part thereof, is disposed substantially within one of the at least one transparent portion or at least one opaque portion, and wherein when gas flow is present and/or the predetermined gas flow rate has been achieved and/or is being maintained, the at least one gas flow signal means, or at least part thereof, is moved to be disposed substantially within the other of the at least one transparent portion or at least one opaque portion.

Preferably the at least one gas flow signal means, or at least part thereof, is biased to a rest position substantially within one of the at least one transparent portion or at least one opaque portion.

In one practical preferred embodiment, the gas flow indicator apparatus includes one gas flow signal means and one opaque portion, wherein it is preferred that the gas flow signal means, or at least part thereof, is biased to a rest position substantially within the opaque portion. In a further practical preferred embodiment, the gas flow indicator apparatus includes one gas flow signal means and one transparent portion, wherein it is preferred that the gas flow signal means, or at least part thereof, is biased to a rest position substantially within the transparent portion. Preferably movement of the gas flow signal means, or at least part thereof, out of the opaque portion or the transparent portion, and substantially into the at least one transparent portion or the at least one opaque portion, indicates that a predetermined minimum gas flow rate has been achieved and/or is being maintained. Preferably said predetermined minimum gas flow rate is 6 L/min.

In a practical preferred embodiment, the gas flow signal means is a bellows device. In an alternative practical preferred embodiment, the gas flow signal means is a piston device. Preferably, in use, gas flows through and/or around the bellows or piston device.

Preferably the gas flow indicator apparatus includes one outlet port for removable or permanent attachment to a gas delivery device, system and/or conduit. It is also preferred that the gas flow indicator apparatus includes one inlet port for receiving gas from a gas supply conduit and/or source.

Preferably the gas flow indicator apparatus further includes at least one ambient air inlet hole for entrainment of ambient air during use thereof.

Preferably the gas flow indicator apparatus further includes means for preventing component parts of the gas flow indicator apparatus from exiting the gas flow chamber and/or for preventing foreign objects from entering into the gas flow chamber.

In a practical preferred embodiment, the gas flow indicator apparatus is for monitoring the flow of gas through, or to, a breathing gas delivery device, system and/or conduit.

According to a further aspect, the present invention provides a breathing apparatus or system including the gas flow indicator apparatus of any one of the preceding paragraphs.

According to yet a further aspect, the present invention provides a breathing gas supply conduit including the gas flow indicator apparatus of any one of the preceding paragraphs.

According to still yet a further aspect, the present invention provides a method of monitoring the delivery of gas to a person's airway, the method comprising the steps of: interposing the flow indicator apparatus of any one of the preceding paragraphs between the distal end or ends of at least one gas supply conduit and at least one gas inlet port of a breathing apparatus, or at least one gas supply conduit connected to the breathing apparatus; and, observing the gas flow indicator apparatus; wherein movement of the at least one gas flow signal means within the gas flow chamber indicates that gas is flowing and/or a minimum predetermined gas flow rate has been achieved.

These and other essential or preferred features of the present invention will be apparent from the description that now follows.

BRIEF DESCRIPTION OF THE DRAWINGS

In order that the invention may be more clearly understood and put into practical effect there shall now be described in detail preferred constructions of gas flow indicator apparatus for gas delivery devices, systems, and/or conduits, in accordance with the invention. The ensuing description is given by way of non-limitative examples only and is with reference to the accompanying drawings, wherein:

FIG. 22 is a side view of the gas flow indicator apparatus of FIGS. 20 & 21, the apparatus shown in a first state which, in use, indicates that there is no gas flow present;

FIG. 23 is a cross-sectional side view of the gas flow indicator apparatus of FIGS. 20 to 22, taken along and in the direction of arrows 23-23 of FIG. 22;

FIG. 24 is a side view of the gas flow indicator apparatus of FIGS. 20 to 23, the apparatus shown in a second state which, in use, indicates that there is gas flow present;

FIG. 25 is a cross-sectional side view of the gas flow indicator apparatus of FIGS. 20 to 24, taken along and in the direction of arrows 25-25 of FIG. 24;

FIG. 34 is a side view of a gas flow indicator apparatus made in accordance with still yet a further preferred embodiment of the present invention, the gas flow indicator apparatus being suitable for removable or permanent attachment to a gas delivery device, system, and/or gas supply conduit, the apparatus shown in a first state which, in use, indicates that there is gas flow present; and, FIG. 35 is a cross-sectional side view of the gas flow indicator apparatus of FIG. 34, taken along and in the direction of arrows 35-35 of FIG. 34.

MODES FOR CARRYING OUT THE INVENTION

Figure 1:
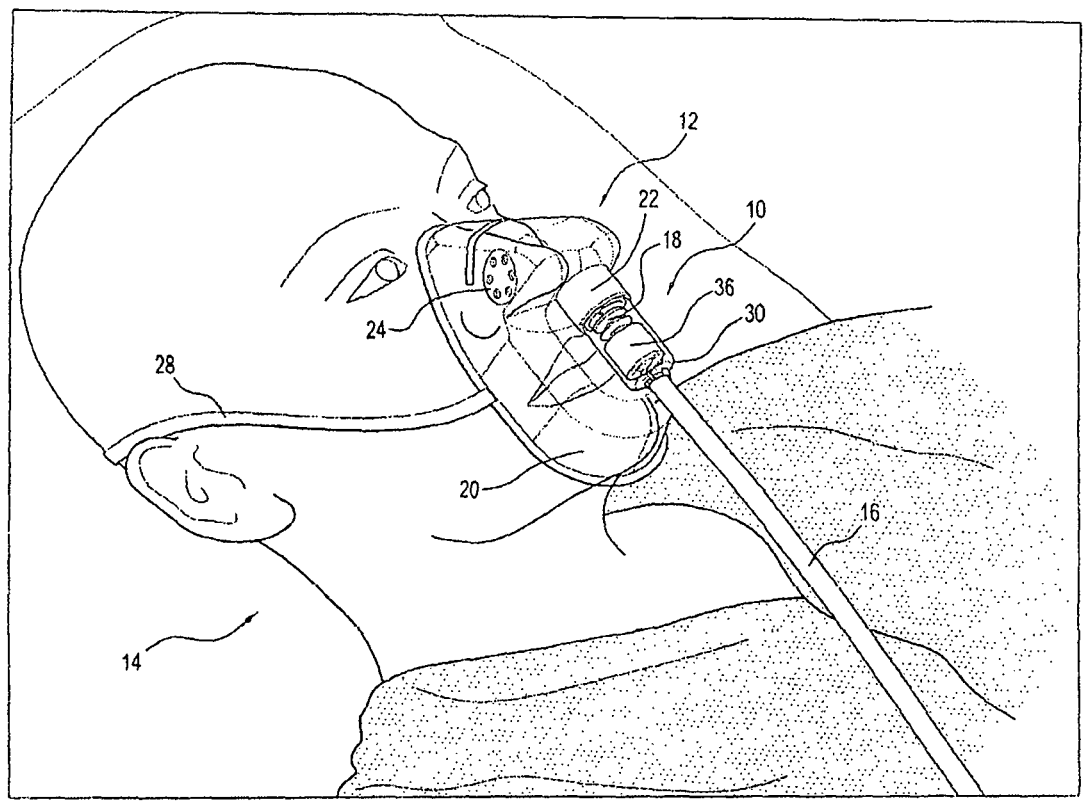
FIG. 1 is perspective view of an exemplary gas delivery device, more particularly a gas delivery mask, incorporating a gas flow indicator apparatus made in accordance with a preferred embodiment of the present invention, the mask shown in use, suitably positioned on the face of a patient, connected to a gas supply system by way of a supply conduit, and having gas flowing therethrough.

In the following detailed description of the invention, reference is made to the drawings in which like reference numerals refer to like elements throughout, and which are intended to show by way of illustration, specific embodiments in which the invention may be practiced. It is to be understood that other embodiments may be utilised, and that structural changes may be made, without departing from the scope and spirit of the invention.

As will be readily apparent from the detailed description that follows, the present invention relates to gas flow indicator apparatus for gas delivery devices, systems, and/or gas supply conduits, and preferably to gas flow indicator apparatus for medical devices, systems and/or conduits that deliver breathing gas(es) to an individual's airway. The gas flow indicator apparatus of the present invention is particularly well suited to medical gas delivery devices or systems such as, for example, masks, nasal cannulas, or bag valve masks ("BVMs"), all being of the type supplied by a flexible conduit with gas from a gas cylinder or gas supply system. The gas flow indicator apparatus providing, in use, a visual indication of the flow of gas to, or through, the gas delivery device or system. Further, and as will be described in detail below, the position of the visual signal means movably disposed within the gas flow indicator apparatus of the present invention may not only indicate that there is gas flowing to, or through, the gas delivery device or system, but may also preferably indicate that a predetermined minimum gas flow rate has been reached and/or is being maintained. The gas flow indicator apparatus can be part of a gas delivery device or system, connected or coupled to a gas delivery device or system, such as, for example, for retrofitting directly thereto, or may be provided or connected/coupled in-line with the gas supply conduit. The provision of the gas flow indicator apparatus of the present invention, either directly connected to a gas delivery device or system (be it permanently connected or otherwise), or proximate to same, such as, for example, in-line with the gas supply conduit adjacent the gas delivery device or system, or connected between the gas supply conduit and the gas delivery device or system, enables medical practitioners, carers, or the likes, or even the patient wearing or using the device or system, to readily and conveniently visually determine whether or not gas is flowing into, or through, a gas delivery device or system. As the gas flow indicator apparatus of the present invention is disposed proximate the patient, not the gas cylinder or supply source, gas flow can be readily monitored without having to focus attention away from the patient. This is of upmost importance in situations where a patient's vital signs must be continually monitored, such as, for example, post surgical or anaesthetic interventions.

In FIG. 1, there is shown a first preferred embodiment of a gas flow indicator apparatus 10 (hereinafter simply referred to as "flow indicator" 10, etc.) made in accordance with the present invention. Flow indicator 10 is shown connected to an exemplary gas delivery device 12, more particularly a gas delivery mask 12 (hereinafter simply referred to as "mask" 12, etc.) for delivering gas(es) to an individual's airway. Flow indicator 10 may be selectively and removably attached to mask 12, or may be permanently attached thereto during production, assembly or otherwise. Mask 12 is shown in use, suitably positioned on the face of a patient 14, connected to a gas supply cylinder or system (not shown), by way of a supply conduit 16, and having gas flowing therethrough. As will be described in further detail below, gas flow into mask 12 is clearly evident by the position of the visual signal means 18, movably disposed within flow indicator 10 of FIG. 1. Further, as visual signal means 18 (hereinafter simply referred to as "signal means" 18, etc.), of flow indicator 10, is fully extended in the embodiment shown in FIG. 1, such also preferably indicates that a minimum gas flow rate has been achieved and/or is being maintained (such as, for example, a desired gas flow rate of about 6 L/min).

Figure 3:
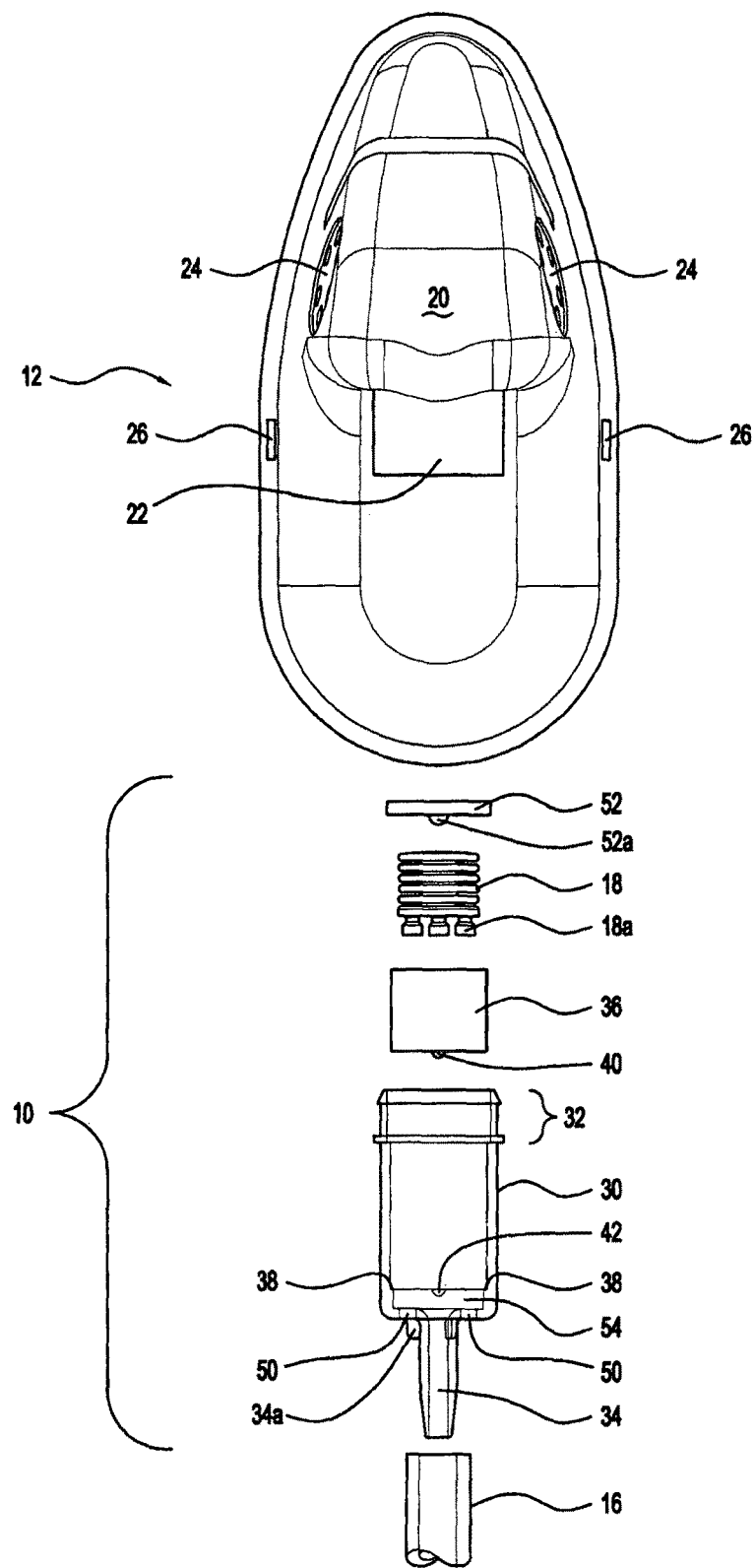
FIG. 3 is an exploded view showing the preferred components of the combined mask and gas flow indicator apparatus of FIG. 1.

FIG. 3 is an exploded view showing the preferred components of the combined mask 12 and flow indicator 10 of FIG. 1. As is typical in the medical industry, here it can be seen that mask 12 is made of a clear plastics material and includes a body 20, which may be resilient or rigid, that is sized to seat over the nose and mouth of a patient 14. Mask 12 includes a gas inlet 22 for receiving gas, and ventilation apertures 24 for venting expiratory gases from mask 12 during use. Mask 12 also includes holes or slits 26 for receiving an elastic strap 28 (see FIG. 1) to assist in maintaining mask 12 on a patient 14 during use. Normally such a mask 12 would be directly connected at its gas supply inlet 22, to a gas supply conduit 16, via an appropriate coupling (not shown). Hence, no flow indicator apparatus of any kind would be provided integral with mask 12. The present invention, however, provides a convenient and useful flow indicator 10 that is disposed intermediately of mask 12 and supply conduit 16. In this way, such a flow indicator 10 can be retrofitted to existing masks 12, either at the production or assembly stage, or by qualified or otherwise persons within a medical environment.

To facilitate the removable or permanent connection of flow indicator 10, to mask 12 and gas supply conduit 16 of FIGS. 1 & 3, flow indicator 10 includes an elongated tubular housing 30 which forms a chamber for gas flow therethrough, having a mask engaging spigot 32 disposed at one end, and a supply conduit engaging spigot 34 disposed at its other end. Housing 30 may comprise a single component (for example, as shown in the preferred embodiments of FIGS. 1 to 19), or may be constructed of multiple components, which together form a combined housing 30 (for example, as shown in the preferred embodiments of FIGS. 20 to 35). Although shown in the drawings as being tubular in shape, it will be appreciated that housing 30, of flow indicator 10, may be of any suitable size and shape as required. The present invention should therefore not be construed as limited to the specific tubular example provided. As can be best seen in FIG. 3, when assembled, mask engaging spigot 32 is received within (or by) gas supply inlet 22 of mask 12, whilst supply conduit engaging spigot 34 is received within (or by) gas supply conduit 16. To prevent supply conduit 16 from abutting against housing 30 (such as, for example, to prevent conduit 16 from blocking ambient air inlet hole(s) 50 of housing 30—as will be described in further detail below), conduit engaging spigot 34 preferably includes at least one projection or shoulder 34*a*, for example three projections 34*a* as shown, which limit upward movement of conduit 16 relative to spigot 34. Although not shown, spigots 32,34, may include ribs or the likes for assisting with the frictional or permanent connection of flow indicator 10 to mask 12 and/or conduit 16. Further, although spigots 32,34 are shown and described as being preferred means of coupling flow indicator 10 to mask 12 and gas supply conduit 16, it will be appreciated that any suitable coupling means could be used and provided in accordance with the invention. Further still, although a single coupling (spigots 32;34) is shown in the drawings, it will be appreciated that more than one coupling could be provided at one or both ends of flow indicator 10. Hence, hereinafter wherever a single spigot, coupling, etc., is shown and described, such should be construed as meaning "at least one" spigot, coupling, etc. Again, it will be appreciated that the need for more than one spigot, coupling, etc., may depend on the gas delivery device or system to which the flow indicator is to be connected to. Accordingly, the present invention should not be construed as limited to any of the specific examples provided.

In the drawings it can be seen that housing 30 of flow indicator 10 is preferably made of a suitable material that includes at least one transparent portion, preferably a plastics material having at least one clear section. That is, housing 30 may be partially transparent, and hence may only provide a transparent window(s), or the likes, for viewing signal means 18, such as, for example, as shown in the preferred embodiments of FIGS. 20 to 35, or may be entirely or substantially transparent, such as, for example, as shown in the preferred embodiments of FIGS. 1 to 19.

In the preferred embodiment shown in FIGS. 1 & 3 (and in the further preferred embodiments shown and described with reference to FIG. 2 and FIGS. 4 to 19), it can be seen that housing 30 of flow indicator 10 is entirely transparent, and is preferably made of a suitable clear plastics material. Given the choice of a fully transparent housing 30 in this instance, disposed within housing 30 is an opaque signal means concealment chamber 36 (hereinafter simply referred to as "concealment chamber" 36, etc.) which is provided to at least substantially conceal signal means 18 during use of flow indicator 10. As is shown in the drawings (more specifically, FIGS. 1 to 19), it is preferred that the concealment of signal means 18, within concealment chamber 36, indicates that there is no gas flowing through flow indicator 10 (and/or that a predetermined gas flow rate has not been achieved). However, it will be appreciated that the reverse operation is also possible (see for example, the preferred embodiment of FIGS. 30 to 33, which will be described in further detail below). That is, the design and position of concealment chamber 36 (if required) and signal means 18, within housing 30, could be altered such that when signal means 18 is concealed within concealment chamber 36, same indicates that gas is flowing through flow indicator 10 (and/or a predetermined gas flow rate has been achieved and/or is being maintained). In such an alternative embodiment, signal means 18 may be visible through housing 30 until such time that gas flow is present and/or a predetermined gas flow rate has been achieved. A skilled person will appreciate suitable constructional changes that could be made to flow indicator apparatus of the present invention in order to achieve such a reverse operation. Accordingly, the present invention should not be construed as limited to the specific preferred operation of flow indicator 10 as shown in the drawings.

In the preferred embodiment of FIGS. 1 & 3, signal means 18 of flow indicator 10 is designed to be visible when gas flow is present within flow indicator 10. Hence, the position of concealment chamber 36, within housing 30, is such that same substantially conceals signal means 18 when no gas flow is present, and/or at least partially conceals signal means 18 when a predetermined gas flow rate has not been achieved.

Concealment chamber 36 may be constructed of any suitable material, preferably a suitable plastics material, which is opaque in its finished form, or which is coated with an opaque material before assembly of flow indicator 10. It will be appreciated that opaque concealment chamber 36 may not be required should housing 30 include an opaque surface or portion integral therewith (see for example, the preferred embodiments of FIGS. 20 to 35, which will be described in further detail below). In other words, housing 30 may be specifically designed such that it provides both a transparent area(s) for easily viewing signal means 18 when, for example, gas is flowing (and/or a sufficient gas flow rate is achieved), and an opaque area(s) for concealing (or at least partially concealing) signal means 18 when, for example, no gas flow is present. Similarly, even if a concealment chamber 36 is utilised, it should be appreciated that concealment chamber 36 need not be entirely opaque. That is, depending on the dimensions of concealment chamber 36 and/or signal means 18, and/or the transparent/opaque nature of housing 30, concealment chamber 36 may only be partially opaque in design. The present invention should therefore not be construed as limited to the specific examples provided.

In its assembled state, in the preferred embodiment shown in FIGS. 1 & 3, concealment chamber 36 is positioned and affixed within housing 30 of flow indicator 10, and sits on a shoulder 38 provided by a narrowing of the internal diameter of housing 30, adjacent conduit engaging spigot 34. To ensure the correct alignment of concealment chamber 36, on shoulder 38, within housing 30, concealment chamber 36 preferably includes at least one alignment lug 40, for example one lug 40 as shown, which is received within a matched depression 42 (or more than one depression, if required) provided on shoulder 38. Concealment chamber 36 can be affixed within housing 30 by any suitable means, such as, for example, by way of a frictional fit, a screw-type fit, or by way of an adhesive.

Figure 9:
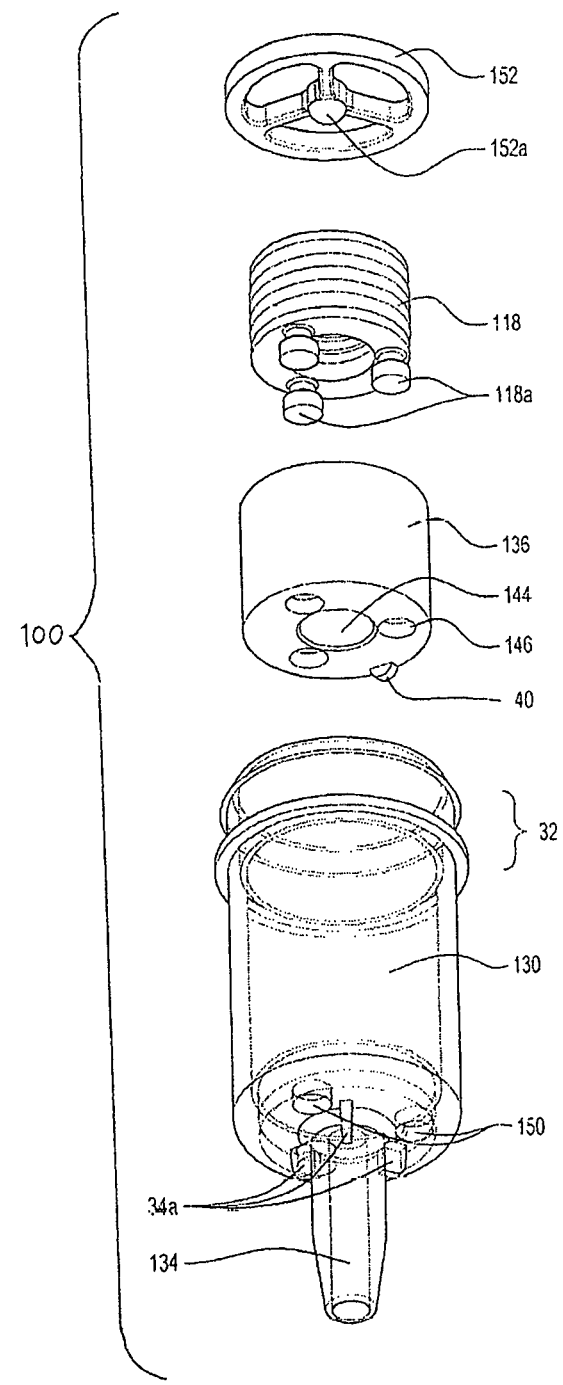

At the base of concealment chamber 36 there is provided a gas inlet hole 44 (not visible in FIGS. 1 & 3, but see, for example, reference numeral 144 in FIG. 9—although it should be appreciated that more than one gas inlet hole(s) 44,144, etc., may be provided) for directing gas into signal means 18. This may be gas provided by: supply conduit 16; ambient air/gas drawn into housing 30 via air inlet hole(s) 50; or, a mixture of gas provided by supply conduit 16 and ambient air/gas drawn into housing 30 via air inlet hole(s) 50. The provision of ambient air, and the mixing thereof with gas supplied by conduit 16, will be discussed in further detail below.

In the preferred embodiment shown in FIGS. 1 & 3, signal means 18 is a bellows device, or part thereof, which is biased to its rest position within (or substantially within) concealment chamber 36. That is, when no gas flow is present, signal means 18 is substantially hidden within concealment chamber 36, and/or is at least partially hidden when a predetermined gas flow rate has not been achieved. Signal means 18 may be constructed of any suitable material, but is preferably constructed of rubber, a rubber compound, or a synthetic non-latex compound having "memory" to expand and contract as required in accordance with the invention. It is also preferred that signal means 18 is constructed of a non-ferrous material so as not to interfere with medical equipment. Signal means 18 is preferably constructed of a material having a bright colour(s), or is coated with a bright coloured material, so that the position of signal means 18 within flow indicator 10 is clearly visible and readily determinant when required. Fluorescent materials or coatings for signal means 18 are especially preferred given the ease of visibility of same. It will be appreciated that only a portion of the preferred bellows device need make up the signal means 18 of the present invention. Hence, only that portion of the bellows device need be brightly coloured or otherwise for ease of visibility within housing 30.

In an alternative embodiment (such as, for example, as shown in the preferred embodiment of FIGS. 30 to 33), wherein the signal means is designed to be visible when no gas flow is present, a dark coloured signal means, such as, for example, a black bellows or piston device, could be suitably disposed within the housing of the flow indicator, and biased to its expanded position relative to the gas supply end of the flow indicator. In such an alternative embodiment, the housing of the flow indicator may include an opaque component or section relative to the gas delivery, device end of the flow indicator, or a concealment chamber could be disposed at the gas delivery device end of the flow indicator in situations where the housing is totally transparent, such that gas flowing into the flow indicator would act upon the signal means, and hence force the signal means into (or at least substantially into) the opaque portion or concealment chamber, and thus, indicate that gas is flowing (and/or a predetermined gas flow rate has been achieved and/or is being maintained). The signal means, whether it be a bellows or piston device, or any other suitable signal means device, could be attached to, for example, the opaque portion, concealment chamber or grill (or any other suitable positioned internal fixing) as required, in order to achieve this alternative construction. Gas acting on the signal means during use of the flow indicator may pass through and/or around the signal means depending on whether holes are provided on the surface of the signal means. In such an alternative embodiment, a transparent portion of the housing relative to the rest or normally expanded position of the black bellows device (i.e. adjacent the gas supply end of the flow indicator) could be fluorescently tinted such that when gas flow is present, and hence when the black signal means moves into, or substantially into, the opaque portion or concealment chamber (and out of, or at least substantially out of, the transparent portion), light shining into the fluorescently tinted transparent portion of the housing would clearly indicate that gas flow is present (and/or a predetermined gas flow rate has been achieved). Of course many other such variations are also possible, and hence same should be construed as being included within the scope of the invention.

Now, turning attention back to the preferred embodiments shown in the drawings, as can be best seen, for example in FIG. 9, bellows signal means 18 (118 in FIG. 9) is preferably attached to concealment chamber 36 (136) by way of a plurality of plugs 18a (118a) which are received in matched holes 46 (146) provided on the base of concealment chamber 36 (136). Although plugs 18a, and holes 46, are provided as a suitable means of attaching signal means 18 to concealment chamber 36 it will be appreciated that any suitable means of attachment may be employed. Hence, the method or means of attachment is not important, but instead what is important is that bellows signal means 18 is affixed at or near its base to concealment chamber 36 (or housing 30, for embodiments which do not utilise a concealment chamber—such as, for example, the preferred embodiments shown in FIGS. 20 to 25 and FIGS. 34 & 35) such that gas entering into bellows signal means 18, via concealment chamber gas inlet hole(s) 44 (or supply conduit engaging spigot 34, if no concealment chamber is provided), causes bellows signal means 18 to expand, and hence, move into a position at which signal means 18 is visible from the exterior of flow indicator 10. In other words, gas entering into signal means 18, via gas inlet hole 44 (and/or spigot 34), moves signal means 18 from its contracted position, whereat it is substantially hidden within concealment chamber 36 (and indicates that no gas flow is present and/or a desired gas flow rate has not been achieved), to an expanded positioned, whereat it is at least partially visible from the exterior of flow indicator 10, through transparent, or partially transparent housing 30 (and indicates that gas flow is present).

To provide a passage for the gas entering into signal means 18 to travel through flow indicator 10 (in embodiments wherein gas is required to travel through signal means 18), and into mask 12 (or other gas delivery device/system 12, or conduit 16), signal means 18 preferably includes at least one hole 48, for example a plurality of holes 48 as shown (see, for example, reference numeral 148 in FIG. 8), disposed on its upper surface, adjacent mask engaging spigot 32. The size, position and/or number of holes 48 being selected based on any number of factors, such as, for example, the type and construction of signal means 18, the materials used to produce signal means 18, and/or the desired travel distance (e.g. expansion) of signal means 18 within flow indicator 10. To clearly illustrate that the size, position and/or number of holes 48 can vary as required, and/or to show that no holes 48 are required in embodiments wherein gas is designed to flow around signal means 18, holes 48 are shown in dashed-lines throughout the drawings. As already discussed, it is preferred that flow indicator 10 of the present invention not only indicates that gas flow is present, but also indicates that a minimum rate of gas flow has been achieved and/or is being maintained at gas delivery device 12, or proximate thereto (e.g. in-line with supply conduit 16, etc.). That said, it is preferred that the size, position and/or number of holes 48 provided on the upper surface of signal means 18 is selected such that when signal means 18 is fully expanded within housing 30 (or otherwise travelled or moved within housing 30, see for example, the embodiments of FIGS. 12 to 19 and FIGS. 26 to 33), such indicates that a minimum predetermined gas flow rate has been achieved. That is, the size, position and/or number of holes 48 is directly proportional to the rate of expansion (or movement) of signal means 18 within flow indicator 10, and hence, directly proportional to the signal means 18 indication of the rate of flow of gas through flow indicator 10. In accordance with a preferred embodiment of the invention, when gas delivery device/system is a mask 12, that predetermined gas flow rate is 6 L/min. Hence, when attached to a mask 12, flow indicator 10 of the present invention provides a convenient tool for medical practitioners, etc., to readily use to determine that gas is flowing, and/or that a minimum gas flow rate (e.g. 6 L/min) has been achieved and/or is being maintained.

An important design feature of flow indicator 10 of the present invention is that even if signal means 18 becomes snagged, or is otherwise prevented from performing its intended visual indication of the flow of gas to, or through, a gas delivery device/system 12, such as, for example, mask 12, gas will still flow through flow indicator 10—by way of hole(s) 48 provided on the upper surface of signal means 18, or around signal means 18 in embodiments wherein no hole(s) 48 are provided. Thus, even if flow indicator 10 stops functioning as intended, gas will still safely flow through and/or to a mask 12, etc.

To limit the upward movement of signal means 18, and/or to prevent component parts of flow indicator 10 from travelling into mask 12 (or other gas delivery device/system 12), and/or component parts of mask 12 or foreign objects (such as fingers) entering into flow indicator 10, flow indicator 10 preferably includes at least one grill or annulus means (hereinafter simply referred to as "grill" 52, etc.) disposed adjacent mask engaging spigot 32. Grill 52 can be any suitable shape, such as, for example, a tri-spoke grill 52 as shown in FIGS. 2 to 9 and FIGS. 12 to 19, or an annulus as shown in FIGS. 20 to 33. As a means of ensuring that hole(s) 48 provided on the upper surface of signal means 18 are not blocked by grill 52 during use of flow indicator 10, at least one protrusion 52*a*, or the likes, may be disposed on the underside surface of grill 52. The size, position and/or number of protrusion(s) 52*a* ideally selected to match the size, position and/or number of hole(s) 48. That is, protrusion(s) 52*a* is/are selected so as not to block (any of) hole(s) 48 during use. When gas is flowing through flow indicator 10, grill 52 and/or protrusion(s) 52*a* provide a convenient barrier for preventing upward movement of signal means 18, whilst also providing a point at which contact with signal means 18 represents, for example, that a desired minimum gas flow rate has been achieved and/or is being maintained. Although the use of a grill 52 and/or grill protrusion(s) 52*a* have been described and is/are shown in the drawings, it should be appreciated that such are not essential to the operation of flow indicator 10 of the present invention. Alternative means of limiting upward movement of signal means 18 (see, for example, the shoulders 262 of FIGS. 10 & 11, or the shoulders 862 of FIGS. 34 & 35) may be provided instead of a grill/protrusion 52,52*a*. Similarly, no such limiting means may be required in some instances. Accordingly, the present invention should not be construed as limited to the specific examples provided.

Figure 2:
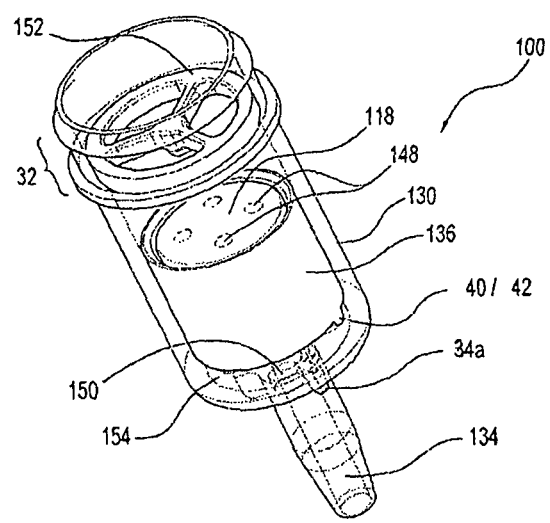
FIG. 2 is a perspective view of a gas flow indicator apparatus made in accordance with a preferred embodiment of the present invention, the gas flow indicator apparatus being suitable for removable attachment to a gas delivery device or system, such as, for example, the mask of FIG. 1, or for permanent attachment thereto during production.

As already briefly discussed above, housing 30 of flow indicator 10 may be provided with at least one ambient air/gas inlet hole(s) 50, for example three holes 50 as shown in FIGS. 1 to 3, provided adjacent supply conduit engaging spigot 34. It will be appreciated that ambient air inlet hole(s) 50 (hereinafter simply referred to as "air inlet hole(s)" 50, etc.) may only be provided in situations where it is acceptable, or desired, to mix supply gas, e.g. supply oxygen, with ambient air, such as, for example, when using a mask 12. Of course in situations where 100% supply gas, e.g. oxygen, is required, or at least desired, such as, for example, with manual resuscitator devices, e.g. bag valve masks, or the likes, flow indicator 10 will not be provided with air inlet hole(s) 50 (see, for example, the embodiments of FIGS. 10 & 11 and FIGS. 34 & 35). Similarly, although hole(s) 50 are shown and described, with reference to FIGS. 1 to 9 and FIGS. 12 to 19, as being provided adjacent supply conduit engaging spigot 34, other arrangements are possible. For example, in the embodiments shown in FIGS. 20 to 33, hole(s) 50 are instead shown positioned adjacent mask engaging spigot 32. A skilled person will appreciate when air inlet hole(s) 50 are or are not required, and where such hole(s) can be disposed. Accordingly, flow indicator 10 of the present invention should not be construed as requiring air inlet hole(s) 50 in order to operate, but instead air inlet hole(s) 50 should be considered optional features (which may be disposed at any suitable location) depending on the application of flow indicator 10.

When air inlet hole(s) 50 are provided, the design of flow indicator 10 is such that atmospheric air is automatically entrained into flow indicator 10, and of course to, or through, gas delivery device/system 12, when gas is supplied by way of supply conduit 16. In one embodiment, as can be seen, for example, in FIG. 3, the specific placement of concealment chamber 36, within housing 30, creates a small void, or gas mixing chamber 54, within housing 30, adjacent supply conduit engaging spigot 34. Thus when supply gas is forced into flow indicator 10, by way of conduit engaging spigot 34, and into mixing chamber 54, a "venturi effect" is created, which results in entrainment of atmospheric air by way of air inlet hole(s) 50. Hence, the result is a mixture of supply gas and atmospheric air, which then travels through and into signal means 18, via gas inlet hole 44 provided on the base of concealment chamber 36, and then onwards through flow indicator 10, to, or through, mask 12 (or other gas delivery device/system/conduit). It will be appreciated that other arrangements of flow indicator 10 may be provided that each enable entrainment of atmospheric air, during use of the flow indicator 10, by way of inlet hole(s) 50. For example, and as will be described in further detail below with reference to the preferred embodiments of FIGS. 20 to 33, instead of mixing chamber 54 being disposed adjacent supply conduit engaging spigot 34, same could instead be provided adjacent mask engaging spigot 32. In such an alternative embodiment, a hole(s) 64 (see for example, 564 in FIGS. 20 to 25) could be provided in grill or annulus 52 so that supply gas (having already travelled through signal means 18) would be forced through hole(s) 64, creating the desired, "venturi effect", and thus, drawing in atmospheric air by way of air inlet hole(s) 50 disposed adjacent mask engaging spigot 32. A skilled person will appreciate many such alternative arrangements. Accordingly, the present invention should not be construed as limited to the specific examples provided.

In FIG. 2 and FIGS. 4 to 9, there is shown a flow indicator 100 made in accordance with a further preferred embodiment of the present invention, flow indicator 100 being suitable for removable attachment to a gas delivery device or system, such as, for example, the mask 12 of FIGS. 1 & 3, or for permanent attachment thereto during production, assembly or otherwise. It will be appreciated that even though flow indicator 100 looks the same as that of flow indicator 10 of FIGS. 1 & 3, flow indicator 100 could be designed and provided for attachment to gas delivery devices/systems other than masks (12). Hence, flow indicator 100 is shown on its own in FIG. 2 and FIGS. 4 to 9 in order to clearly illustrate that flow indicator apparatus of the present invention may be attached to any suitable gas delivery device or system (12), including non-medical gas delivery devices or systems.

In FIG. 2 is can be clearly seen that when no gas flow is present, signal means 118 is substantially hidden within concealment chamber 136 of flow indicator 100. That is, only the upper surface of signal means 118, having hole(s) 148, is preferably visible upon an inspection of flow indicator 100.

Figure 4:
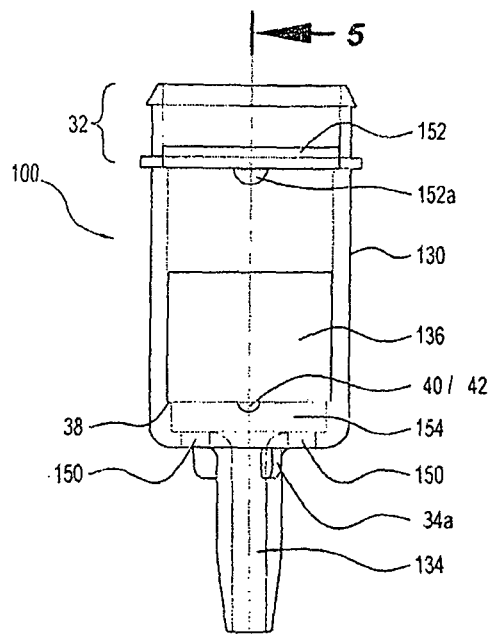
FIG. 4 is a side view of the gas flow indicator apparatus of FIG. 2, the apparatus shown in a first state which, in use, indicates that there is no gas flow present.
Figure 5:
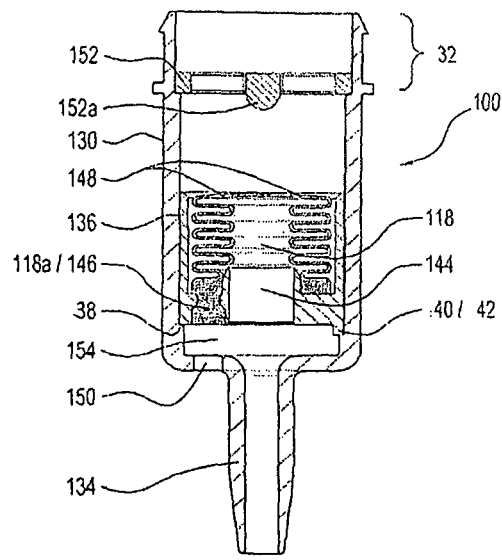
FIG. 5 is a cross-sectional side view of the gas flow indicator apparatus of FIGS. 2 & 4, taken along and in the direction of arrows 5-5 of FIG. 4.

Reference will now be made to FIGS. 4 to 7, in an effort to clearly demonstrate the preferred operation, and use, of flow indicator 100 of the present invention. In FIGS. 4 & 5, flow indicator 100 is shown in a first state which, in use, indicates that there is no gas flow present (and/or a desired gas flow rate has not been achieved). Whereas, in FIGS. 6 & 7, flow indicator 100 is shown in a second state which, in use, indicates that there is gas flow present (and/or a minimum gas flow rate has been achieved and/or is being maintained).

In FIGS. 4 & 5, it can be seen that when no gas flow is present (and/or no minimum desired gas flow rate is achieved) within flow indicator 100, signal means 118 is substantially hidden within concealment chamber 118. In this first state of operation of flow indicator 100, the design of transparent (or substantially or partially transparent) housing 130 is such that when no gas flow is present, a medical practitioner, or the likes, can clearly see straight through flow indicator 100. Hence, no (preferably bright coloured) signal means 118 projects out of concealment chamber 136, and into the void provided within housing 130 for travel (or expansion) of signal means 118. In such circumstances, during use of flow indicator 100, and any associated gas delivery device/system (not shown), a medical practitioner, etc., will be able to readily determine with a quick glance, whether or not gas flow is present (and/or a minimum desired gas flow rate has been achieved).

Figure 6:
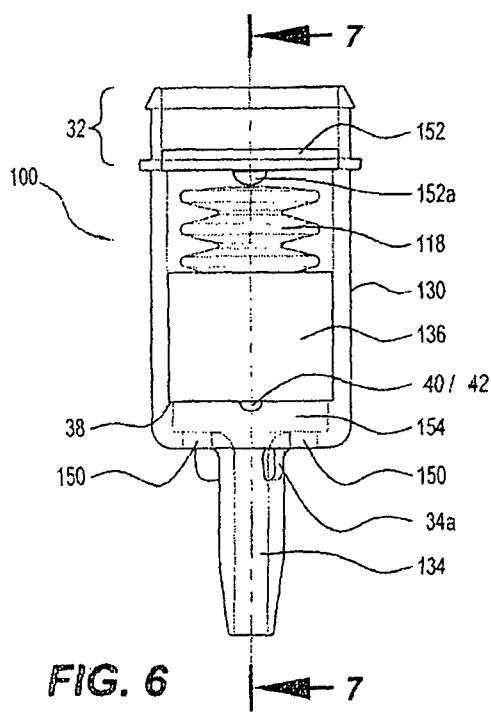
FIG. 6 is a side view of the gas flow indicator apparatus of FIGS. 2, 4 & 5, the apparatus shown in a second state which, in use, indicates that there is gas flow present.
Figure 7:
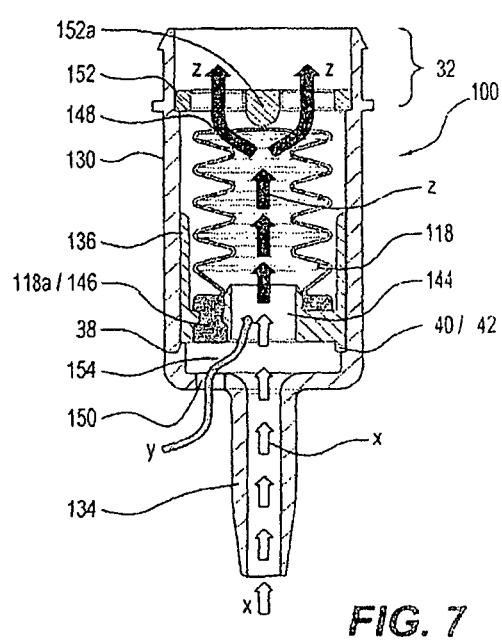
FIG. 7 is a cross-sectional side view of the gas flow indicator apparatus of FIG. 2 and FIGS. 4 to 6, taken along and in the direction of arrows 7-7 of FIG. 6.
Figure 8:
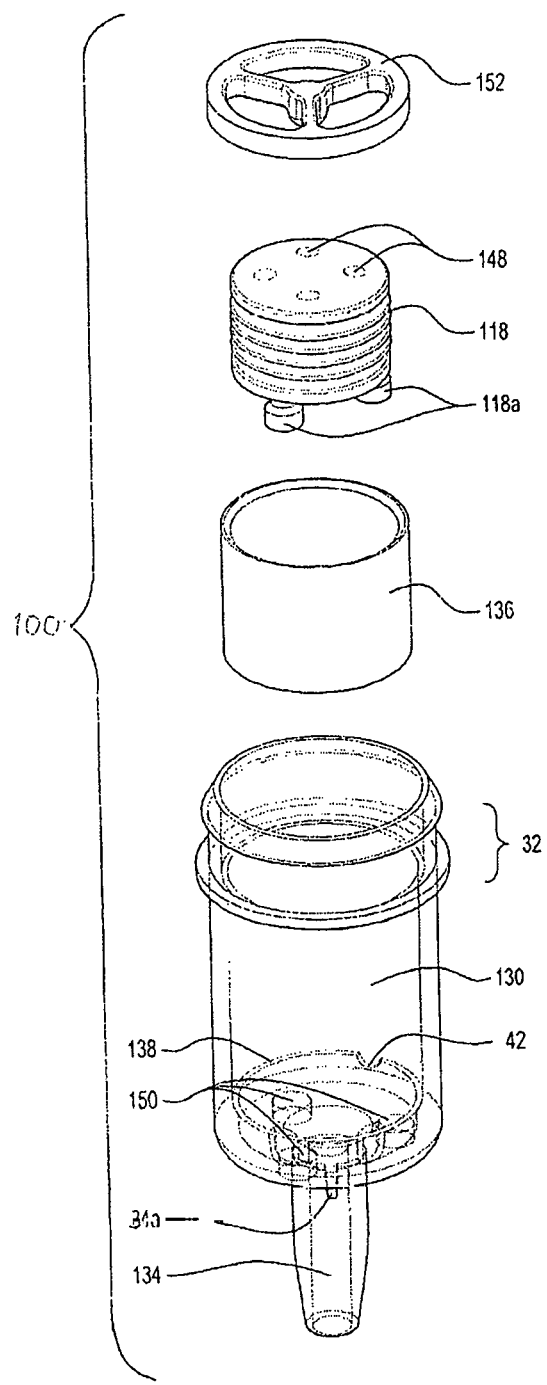
FIGS. 8 & 9 are exploded perspective views showing the preferred components of the gas flow indicator apparatus of FIG. 2 and FIGS. 4 to 7.

In FIGS. 6 & 7, however, it can be seen that when gas flow is present (and/or a minimum desired gas flow rate has been achieved) within flow indicator 100, signal means 118 has travelled (or expanded in the case of preferred bellows signal means 118) out of concealment chamber 136, and is clearly visible from the exterior of flow indicator 100. Hence, in this second state of operation of flow indicator 100, the design of transparent (or substantially or partially transparent) housing 130 is such that when gas flow is present, a medical practitioner, or the likes, can clearly see signal means 118 from the exterior of flow indicator 100. That is, when gas flow is present (and/or when a desired minimum gas flow rate has been achieved), signal means 118 (which is preferably bright coloured) fills the void provided within housing 130 for travel (or expansion) thereof. In such circumstances, during use of flow indicator 100, and any associated gas delivery device/system (not shown), a medical practitioner, etc., will be able to readily determine with a quick glance, that gas is flowing. Furthermore, and in accordance with a preferred aspect of the invention, as signal means 118 in FIGS. 6 & 7 is shown having fully travelled (or expanded) within flow indicator 100, to be in contact with grill protrusion 152a, such also indicates that a minimum desired gas flow rate has been achieved (such as, for example, 6 L/min).

Referring to FIG. 7, it can be seen that when gas x is supplied to flow indicator 100, by way of a supply conduit (not shown), connected to conduit engaging spigot 134, and when preferred air inlet hole(s) 150 are provided, atmospheric air y is entrained into flow indicator 100, through air inlet hole(s) 150, by virtue of the "venturi effect" created at or within mixing chamber 154. Hence, the result is a gas mixture z, being a combination of supply gas x and atmospheric air y, which passes through flow indicator 100, via concealment chamber hole(s) 144, signal means hole(s) 148 and grill 152.

Figures 10, 11:
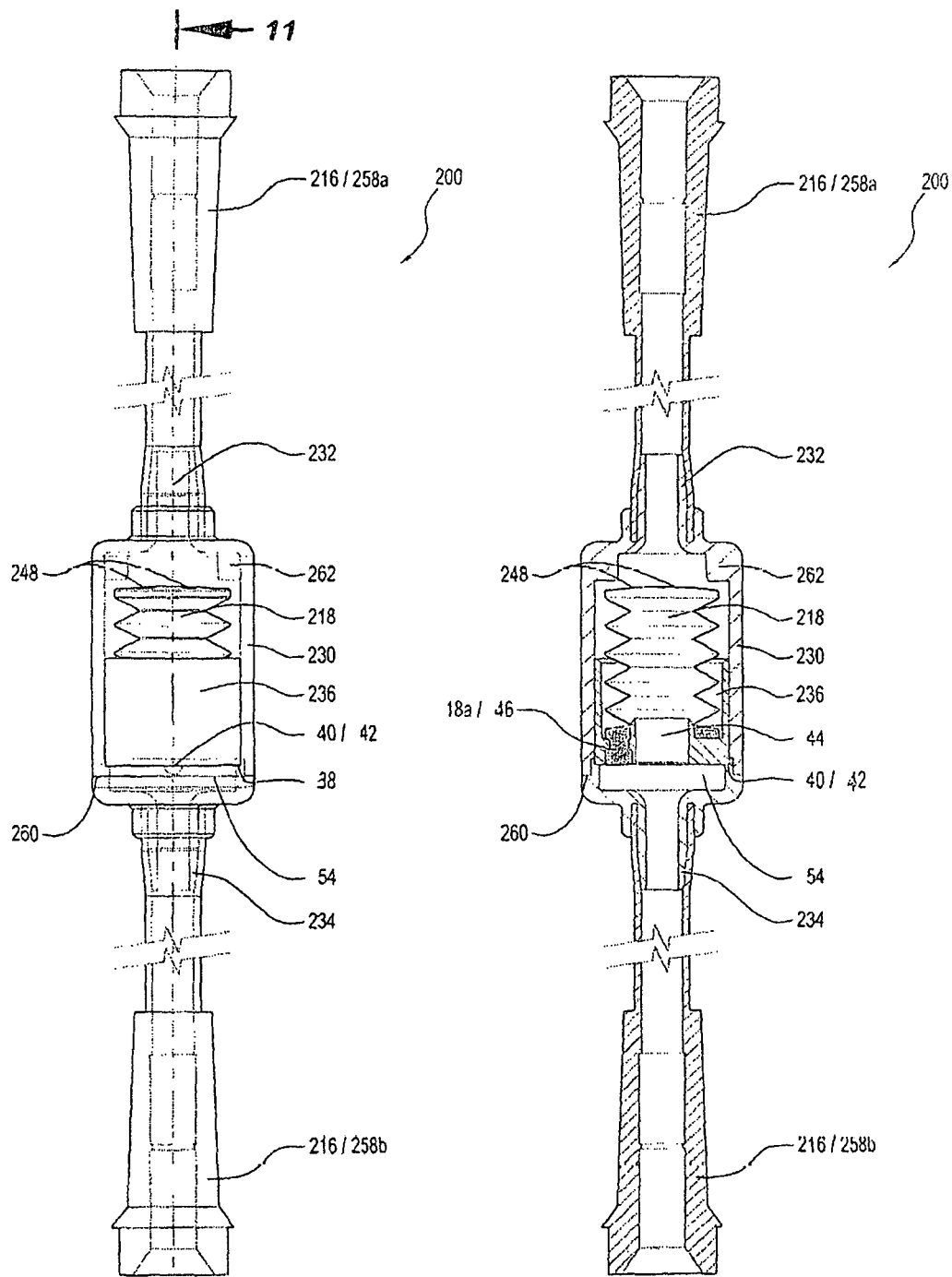
FIG. 10 is a side view of a gas flow indicator apparatus made in accordance with a further preferred embodiment of the present invention, the gas flow indicator apparatus being suitable for removable or permanent attachment to a gas delivery device, system, and/or gas supply conduit.
FIG. 11 is a cross-sectional side view of the gas flow indicator apparatus of FIG. 10, taken along and in the direction of arrows 11-11 of FIG. 10.

In FIGS. 10 to 11, there is shown a flow indicator 200 made in accordance with yet a further preferred embodiment of the present invention, flow indicator 200 also being suitable for removable attachment to a gas delivery device or system, such as, for example, the mask 12 of FIGS. 1 & 3, or a manual resuscitator device (not shown), e.g. a bag valve mask or "BVM", or for permanent attachment thereto during production, assembly or otherwise. Flow indicator 200 may also be disposed in-line with supply conduit (16), such as, for example, by frictional or permanent splicing. Alternatively, flow indicator 200 may be supplied at any suitable length such that same replaces or becomes the supply conduit (16)—having flow indicator 200 combined therewith. Further, it will be appreciated that flow indicator 200 could be designed and provided for attachment to gas delivery devices/systems other than masks (12), BVMs (12), or supply conduits (16). Accordingly, flow indicator 200 of the present invention may be attached to any suitable gas delivery device, system and/or supply conduit, including non-medical gas delivery devices, systems and/or supply conduits.

In one preferred form, flow indicator 200 may be provided for removable or permanent attachment to a BVM, or "AMBU" bag or mask (not shown). As such gas delivery devices are already configured to entrain atmospheric air, when required, flow indicator 200 need not be provided with atmospheric air inlet hole(s). Hence, no such air inlet hole(s) are shown in FIGS. 10 & 11 (it will be appreciated, however, that for other in-line or otherwise applications of flow indicator 200, air inlet hole(s) may be provided). Instead, flow indicator 200 is this time purposely constructed to supply 100% gas from a supply conduit 216. In other words, flow indicator 200 is preferably a closed circuit system. In the embodiment shown in FIGS. 10 & 11, attachment to a gas delivery device or system (not shown) could be provided by way of direct connection of coupling 258a (at the distal end of flow indicator 200, proximate the gas delivery device or system) to a gas inlet (not shown) of the gas delivery device or system. Alternatively, flow indicator 200 could be spliced (be it permanently or otherwise) in gas supply conduit 216. As a further alternative, embodiment, flow indicator 200 may, with integral supply conduit 216 and couplings 258a,258b, simply replace what would otherwise be a standard supply conduit, with a supply conduit incorporating flow indicator 200 (i.e. becoming a combined supply conduit/flow indicator 200 system). A skilled person will appreciate such variations and/or further alternatives, and hence, the present invention should be construed as including within its scope all possible variations/alternatives. To illustrate all possible alternatives discussed above, in FIGS. 10 & 11, standard supply and distal end spigots 234,232 (this time with no conduit limiting projection(s) or shoulder, since no air inlet hole(s) are present which may be blocked by supply conduit 216), are shown, along with supply conduits 216 and couplings 258a,258b. Further, supply conduits 216 are shown with sectioning to indicate that they could be of indefinite length.

No matter how flow indicator 200 is connected to a gas delivery device or system (not shown), or gas supply conduit 216, flow indicator 200 operates in substantially the same manner as that of flow indicators 10,100, of FIGS. 1 to 9, and only varies in respect of minor constructional changes, and operation (including those differences already discussed in the preceding paragraph). First of all, housing 230 is formed in two parts (but could be formed of more than two parts), and joined during production or assembly, at joint 260. It will be appreciated that joint 260, or more than one joint (not shown), could be disposed at any suitable location on housing 230. The other major difference is the absence of a grill, that is, this time instead of a grill, flow indicator 200 is provided with a limiting shoulder or shoulders 262 formed as part of housing 230. In use, shoulder(s) 262 act in the same fashion as that of a grill, i.e. by limiting upward movement of signal means 218, within housing 230. Obviously, in view of the provision of shoulder(s) 262, the size, position and number of hole(s) 248 on the upper surface of signal means 218, are varied accordingly so as to prevent hole(s) 248 occlusion. It will of course be appreciated that a grill (not shown) could be provided instead of limiting shoulder(s) 262. Aside from these constructional differences, flow indicator 200 operates in much the same fashion as that of flow indicators 10,100, of FIGS. 1 to 9. That is, when gas flow is present (and/or a minimum desired gas flow rate has been achieved and/or maintained) signal means 218 travels out of concealment chamber 236, and into clear sight from, the exterior of flow indicator 200. Again, signal means 218 is preferably brightly coloured for ease of visibility in use.

In FIGS. 12 to 15, there is shown a flow indicator 300 made in accordance with still yet a further preferred embodiment of the present invention, flow indicator 300 also being suitable for removable attachment to a gas delivery device or system, such as, for example, the mask 12 of FIGS. 1 & 3, or for permanent attachment thereto during production, assembly or otherwise. It will be appreciated that flow indicator 300 could be designed and provided for attachment to gas delivery devices/systems other than masks (12). Hence, flow indicator 300 of the present invention may be attached to any suitable gas delivery device or system (12), including non-medical gas delivery devices or systems.

Figure 12:
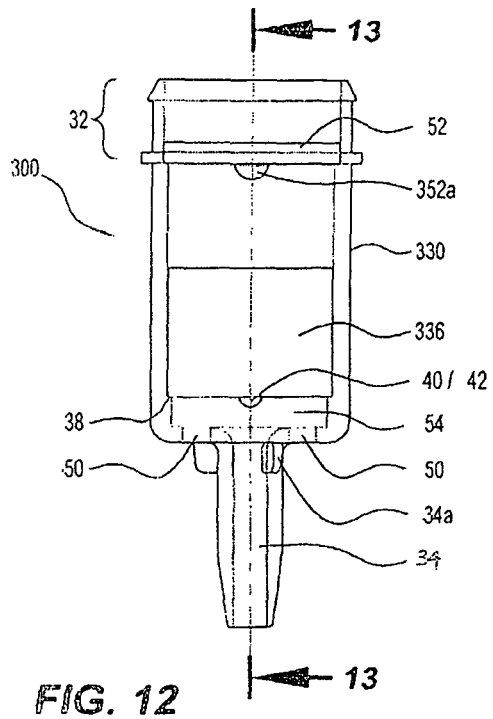
FIG. 12 is a side view of a gas flow indicator apparatus made in accordance with yet a further preferred embodiment of the present invention, the gas flow indicator apparatus being suitable for removable or permanent attachment to a gas delivery device or system, such as, for example, the mask of FIG. 1, the apparatus shown in a first state which, in use, indicates that there is no gas flow present.
Figure 13:
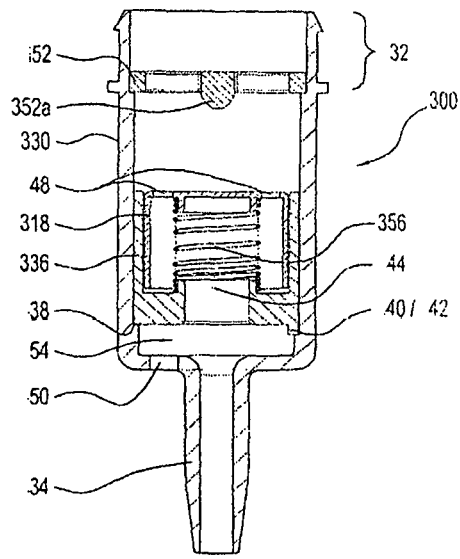
FIG. 13 is a cross-sectional side view of the gas flow indicator apparatus of FIG. 12, taken along and in the direction of arrows 13-13 of FIG. 12.

In FIGS. 12 & 13, flow indicator 300 is shown in a first state which, in use, indicates that there is no gas flow present (and/or a desired gas flow rate has not been achieved). Whereas, in FIGS. 14 & 15, flow indicator 300 is shown in a second state which, in use, indicates that there is gas flow present (and/or a minimum gas flow rate has been achieved and/or is being maintained).

Figure 14:
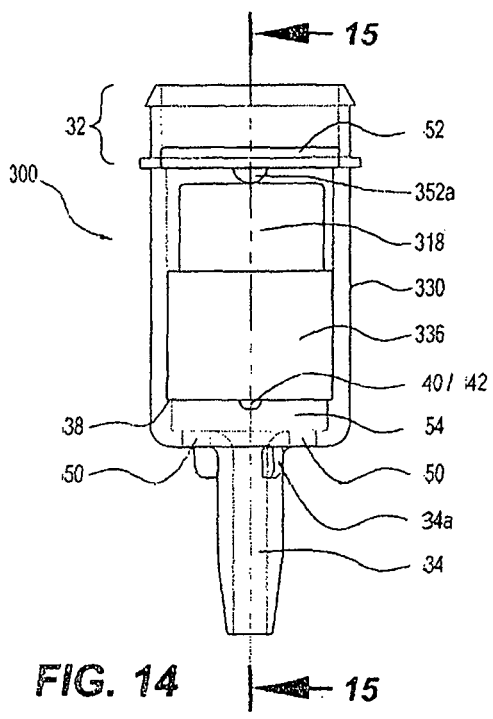
FIG. 14 is a side view of the gas flow indicator apparatus of FIGS. 12 & 13, the apparatus shown in a second state which, in use, indicates that there is gas flow present.
Figure 15:
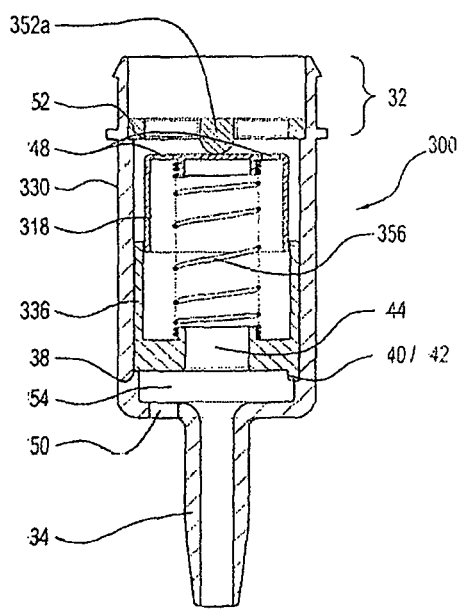
FIG. 15 is a cross-sectional side view of the gas flow indicator apparatus of FIGS. 12 to 14, taken along and in the direction of arrows 15-15 of FIG. 14.

Flow indicator 300 operates in substantially the same manner as that of flow indicators 10,100,200 of FIGS. 1 to 11, and only varies in respect of the construction and operation of signal means 318 (and its attachment to concealment chamber 336). That is, in FIGS. 12 to 15, signal means 318 is not a bellows device as in the case of flow indicators 10,100,200 of FIGS. 1 to 11, but is instead a piston signal means 318 which moves in and out concealment chamber 336 against/with the action of a suitable biasing means 356, for example, a suitable spring 356 as shown. Spring 356 can be made of any suitable material, but is preferably metal or plastic depending on the intended use of flow indicator 300. For example, in situations where flow indicator 300 is required to be worn by a patient having an MRI (Magnetic Resonance Imaging), spring 356 would be made of a plastics, or other non-ferrous material, such that same would not interfere with the MRI, or similar, procedure and/or medical equipment. Although not shown in the drawings, instead of a spring 356, biasing means 356 could be a bellows device, preferably constructed of a non-ferrous material, which achieves the same or a similar function to that of a spring, i.e. it biases piston means 318 to its desired rest position. A skilled person will appreciate this and further alternative arrangements of biasing means 356, and as such, the present invention should be construed as including within its scope any suitable biasing means 356 which is able to urge piston means 318, etc., to its desired rest position. In the present embodiment, it is preferred that signal means 318 is biased to its hidden, or partially/substantially hidden, state within concealment chamber 336, by virtue of spring 356, etc. Further, as signal means 318 is not a bellows device, signal means 318 is not directly connected to concealment chamber 336, but instead is connected to spring 356, which is in turn connected to concealment chamber 336. The size and construction of piston signal means 318 is such that same cannot travel out of alignment with concealment chamber 336 by virtue of the fact that grill protrusion(s) 352a prevents upward movement thereof (as can be seen in FIGS. 14 & 15). Aside from these constructional differences, flow indicator 300 operates in much the same fashion as that of flow indicators 10,100,200, of FIGS. 1 to 11. That is, when gas flow is present (and/or a minimum desired gas flow rate has been achieved and/or maintained) piston signal means 318 travels out of concealment chamber 336, and into clear sight from the exterior of flow indicator 300. Again, signal means 318 is preferably brightly coloured for ease of visibility in use.

Although not shown in FIGS. 12 to 15, to assist with the alignment and/or movement of piston means 318 within housing 330, the internal surface of housing 330 may be provided with vertical ribs, or other similar protrusions, which limit horizontal movement of piston means 318 during use of flow indicator 300. That is, vertical ribs, etc. (not shown), could be provided to guide the movement of piston means 318 during use of flow indicator 300. Such vertical ribs, etc. (not shown), could also be provided in embodiments where gas is required to flow around signal means 318, instead of, or in addition to, flowing through signal means 318. That is, the provision of vertical ribs, etc. (not shown), would provide convenient channels for the passage of gas flowing through flow indicator 300.

Further still, although not shown in FIGS. 12 to 15, the orientation of piston means 318 could be reversed. That is, instead of being an inverted U-shaped (when viewed in cross-section—hereinafter where ever "U-shaped" is stated, same is referring to the cross-sectional profile of the signal means) piston means 318, as shown in FIGS. 12 to 15, same could be disposed in an upright U-shaped configuration, which may require a smaller biasing means 356. FIGS. 30 to 33, show an upright U-shaped configuration of a piston signal means (718). In that embodiment, the biasing means (756) is disposed adjacent mask engaging spigot (732), but of course, the biasing means could be disposed adjacent conduit engaging spigot (734), if desired. A skilled person will appreciate many such variations within the scope of the invention herein described. Accordingly, the present invention should not be construed as limited to any specific embodiment provided and/or shown in the drawings.

In FIGS. 16 to 19, there is shown a flow indicator 400 made in accordance with still yet a further preferred embodiment of the present invention, flow indicator 400 also being suitable for removable attachment to a gas delivery device or system, such as, for example, the mask 12 of FIGS. 1 & 3, or for permanent attachment thereto during production, assembly or otherwise. It will be appreciated that flow indicator 400 could be designed and provided for attachment to gas delivery devices/systems other than masks (12). Hence, flow indicator 400 of the present invention may be attached to any suitable gas delivery device or system (12), including non-medical gas delivery devices or systems.

Figure 16:
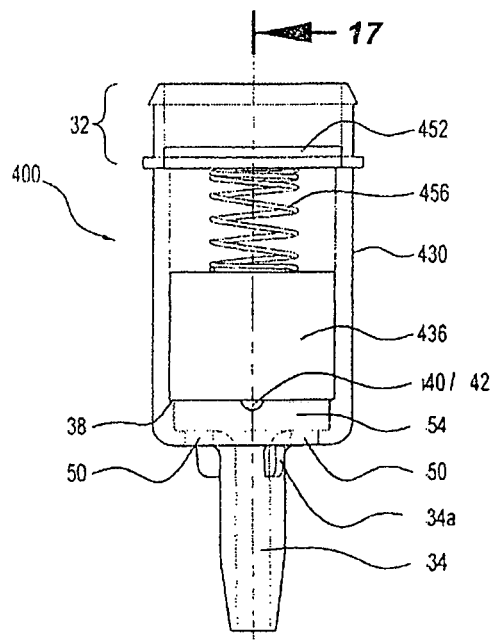
FIG. 16 is a side view of a gas flow indicator apparatus made in accordance with still yet a further preferred embodiment of the present invention, the gas flow indicator apparatus being suitable for removable or permanent attachment to a gas delivery device or system, such as, for example, the mask of FIG. 1, the apparatus shown in a first state which, in use, indicates that there is no gas flow present.
Figure 17:
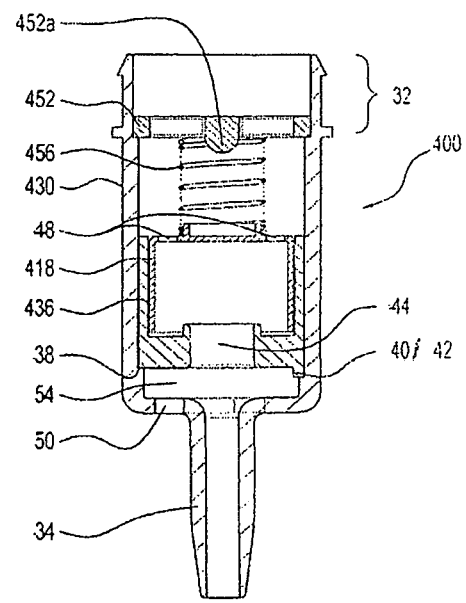
FIG. 17 is a cross-sectional side view of the gas flow indicator apparatus of FIG. 16, taken along and in the direction of arrows 17-17 of FIG. 16.

In FIGS. 16 & 17, flow indicator 400 is shown in a first state which, in use, indicates that there is no gas flow present (and/or a desired gas flow rate has not been achieved). Whereas, in FIGS. 18 & 19, flow indicator 400 is shown in a second state which, in use, indicates that there is gas flow present (and/or a minimum gas flow rate has been achieved and/or is being maintained).

Figure 18:
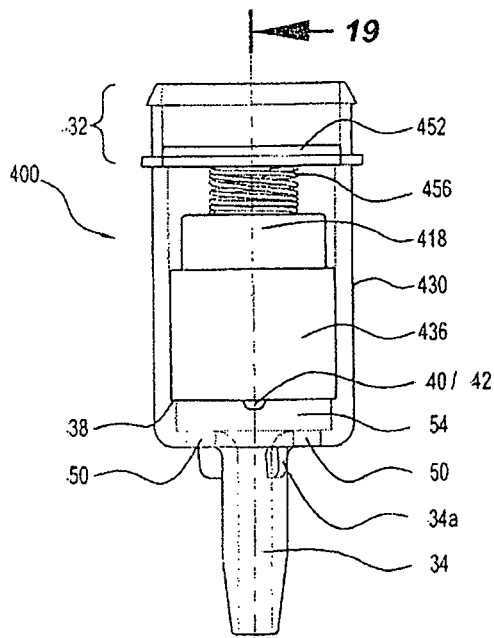
FIG. 18 is a side view of the gas flow indicator apparatus of FIGS. 16 & 17, the apparatus shown in a second state which, in use, indicates that there is gas flow present.
Figure 19:
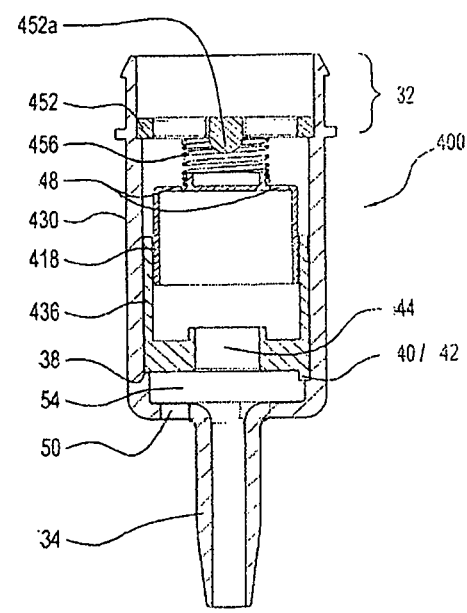
FIG. 19 is a cross-sectional side view of the gas flow indicator apparatus of FIGS. 16 to 18, taken along and in the direction of arrows 19-19 of FIG. 18.
Figures 20, 21:
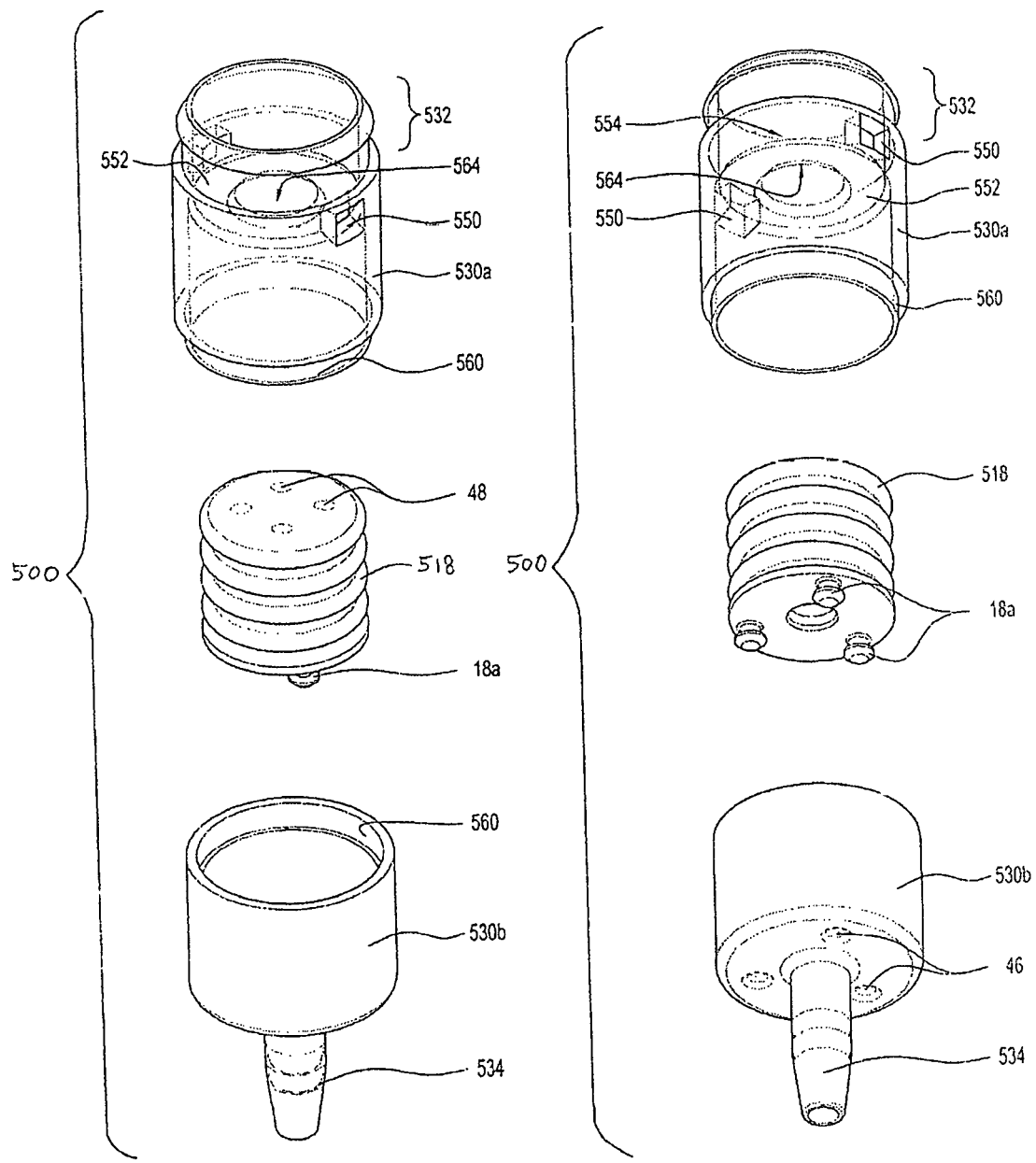
FIGS. 20 & 21 are exploded perspective views showing the preferred components of a gas flow indicator apparatus made in accordance with still yet a further preferred embodiment of the present invention, the gas flow indicator apparatus being suitable for removable or permanent attachment to a gas delivery device or system, such as, for example, the mask of FIG. 1.

Flow indicator 400 operates in substantially the same manner as that of flow indicator 300 of FIGS. 12 to 15, and only varies in respect of the positioning of biasing means 456, for example, spring 456 as shown (and again, the attachment of signal means 418 to concealment chamber 436). That is, in FIGS. 16 to 19, spring 456 is positioned externally of concealment chamber 436, as opposed to internally of concealment chamber 336 of flow indicator 300 of FIGS. 12 to 15. Further, given the preferred position of spring 456, signal means 418 is this time not at all connected to concealment chamber 436, but instead is connected to spring 456, which is in turn connected to, and/or acts upon, grill 452. Again, the size and construction of piston signal means 418 is such that same cannot travel out of alignment with concealment chamber 436 by virtue of the fact that the maximum compression of spring 456 prevents upward movement thereof (as can be seen in FIGS. 18 & 19). In view of this constructional difference, although shown in FIGS. 16 to 19, grill protrusion(s) 452a may not be required given the maximum possible travel of piston signal means 418 within housing 430, by virtue of the position and action of spring 456. Aside from these constructional differences, flow indicator 400 operates in much the same fashion as that of flow indicators 10,100,200,300, of FIGS. 1 to 15. That is, when gas flow is present (and/or a minimum desired gas flow rate has been achieved and/or maintained) piston signal means 418 travels out of concealment chamber 436, and into clear sight from the exterior of flow indicator 400. Again, signal means 418 is preferably brightly coloured for ease of visibility in use.

Although not shown in FIGS. 16 to 17, flow indicator 400 could be varied in many ways similar to that previously described with reference to flow indicators 10 to 300. For example, biasing means 456 could be a bellows device instead of a spring, preferably constructed of a dull or dark coloured material so as to contrast against a preferred bright coloured signal means 418. Further, the alignment of piston means 418 could be reversed so that same is disposed in an upright U-shaped configuration, instead of an inverted U-shaped configuration. Further still, vertical ribs, channels, or other protrusions, etc. (none of which are shown in FIGS. 16 to 19), could be provided in order to assist with the movement of piston means 418 and/or to provide a passage for gas flow around piston means 418. These and other variations will be appreciated by a skilled person, and as such, the present invention should not be construed as limited to the specific examples shown and described.

In FIGS. 20 to 25, there is shown a flow indicator 500 made in accordance with still yet a further preferred embodiment of the present invention, flow indicator 500 also being suitable for removable attachment to a gas delivery device or system, such as, for example, the mask 12 of FIGS. 1 & 3, or for permanent attachment thereto during production, assembly or otherwise. It will be appreciated that flow indicator 500 could be designed and provided for attachment to gas delivery devices/systems other than masks (12). Hence, flow indicator 500 of the present invention may be attached to any suitable gas delivery device or system (12), including non-medical gas delivery devices or systems.

In FIGS. 22 & 23, flow indicator 500 is shown in a first state which, in use, indicates that there is no gas flow present (and/or a desired gas flow rate has not been achieved). Whereas, in FIGS. 24 & 25, flow indicator 500 is shown in a second state which, in use, indicates that there is gas flow present (and/or a minimum gas flow rate has been achieved and/or is being maintained).

Flow indicator 500 operates in substantially the same manner as that of flow indicators 10,100,200,300,400 of FIGS. 1 to 19, and varies firstly in respect of the construction of housing 530. That is, in FIGS. 20 to 25, housing 530 is constructed of multiple components (for example, two components as shown), which together form a combined housing 530. More specifically, in the embodiment provided in FIGS. 20 to 25 it can be seen that housing 530 comprises two components, a first transparent component 530a, preferably made of a suitable clear plastics material, and a second opaque component 530b, preferably made of a suitable opaque plastics material, or coated with an opaque material or covering. Housing components 530a,530b, can be joined during production or assembly, at joint 560, using any suitable means or technique. It will be appreciated that joint 560, or more than one joint (not shown), could be disposed at any suitable location(s) on housing 530.

Given that housing 530, of flow indicator 500, comprises an opaque portion 530b integral therewith, an opaque concealment chamber (36) is not required in this preferred embodiment. Instead, opaque housing component 530b effectively becomes the concealment chamber of flow indicator 500, and therefore acts in the same manner. That is, housing 530 is specifically designed such that it provides both a transparent portion 530a for easily viewing signal means 518 when gas is flowing (and/or a sufficient gas flow rate is achieved), and an opaque portion 530b for concealing (or at least partially concealing) signal means 518 when no gas flow is present.

Other major differences concerning flow indicator 500 of FIGS. 20 to 25, as compared to flow indicators 10,100,200, 300,400, of FIGS. 1 to 19, is the positioning of air inlet hole(s) 550, the location of mixing chamber 554, and the type of grill or annulus 552. That is, this, time both air inlet hole(s) 550 and mixing chamber 554 are located adjacent mask engaging spigot 532, instead of supply conduit engaging spigot 534 as in the case of flow indicators 10,100,200, 300,400, of FIGS. 1 to 19. Further, this time instead of having a tri-spoke grill (52) which is preferably constructed as a separate component for attachment to flow indicator 10,100,300,400, during production of assembly thereof, an annulus 552 is provided which is preferably formed integral with housing component 530a during injection moulding, or the likes. The provision and design of annulus 552 provides a convenient hole(s) 564 for forcing supply gases (having already travelled through signal means 518) into mixing chamber 554, thus creating the desired "venturi effect", which in-turn draws in the required atmospheric air by way of air inlet hole(s) 550.

Aside from these constructional differences, flow indicator 500 operates in much the same fashion as that of, for example, flow indicators 10,100, of FIGS. 1 to 9. That is, given that flow indicators 10,100,500 all share a bellows device (signal means 18,118,518), when gas flow is present (and/or a minimum desired gas flow rate has been achieved and/or maintained) bellows signal means 518 travels out of opaque housing component 530b, and into transparent housing component 530a, and thus into clear sight from the exterior of flow indicator 500. Again, signal means 518 is preferably brightly coloured for ease of visibility in use.

In FIG. 25, it can be seen that when gas x is supplied to flow indicator 500, by way of a supply conduit (not shown), connected to conduit engaging spigot 534, and when preferred air inlet hole(s) 550 are provided adjacent mask engaging spigot 532, atmospheric air y is entrained into flow indicator 500, through air inlet hole(s) 550, by virtue of the "venturi effect" created at or within mixing chamber 554 as supply gas x is forced through annulus hole(s) 564. Hence, the result is a gas mixture z, being a combination of supply gas x and atmospheric airy, which exits flow indicator 500, via mask engaging spigot 532.

Although not shown in FIGS. 20 to 25, flow indicator 500 could be varied in many ways similar to that previously described with reference to flow indicators 10 to 400. For example, the alignment of bellows means 518 could be reversed so that same is affixed within housing 530 adjacent mask engaging spigot 532 (for example, affixed to annulus 552), instead of at conduit engaging spigot 534. Further, vertical ribs, channels, or other protrusions, etc. (none of which are shown in FIGS. 20 to 25), could be provided in order to assist with the movement of bellows means 518 and/or to provide a passage for gas flow around bellows means 518. These and other variations will be appreciated by a skilled person, and as such, the present invention should not be construed as limited to the specific examples shown and described.

In FIGS. 26 to 29, there is shown a flow indicator 600 made in accordance with still yet a further preferred embodiment of the present invention, flow indicator 600 also being suitable for removable attachment to a gas delivery device or system, such as, for example, the mask 12 of FIGS. 1 & 3, or for permanent attachment thereto during production, assembly or otherwise. It will be appreciated that flow indicator 600 could be designed and provided for attachment to gas delivery devices/systems other than masks (12). Hence, flow indicator 600 of the present invention may be attached to any suitable gas delivery device or system (12), including non-medical gas delivery devices or systems.

Figure 26:
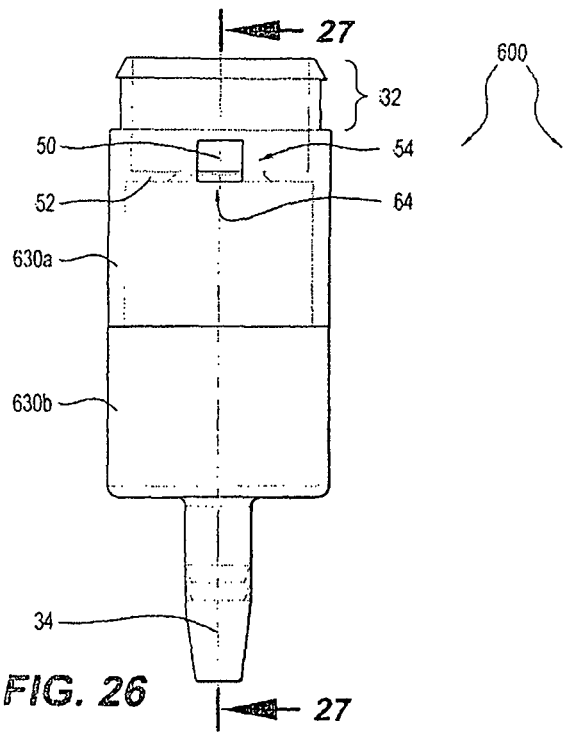
FIG. 26 is a side view of a gas flow indicator apparatus made in accordance with still yet a further preferred embodiment of the present invention, the gas flow indicator apparatus being suitable for removable or permanent attachment to a gas delivery device or system, such as, for example, the mask of FIG. 1, the apparatus shown in a first state which, in use, indicates that there is no gas flow present.
Figure 27:
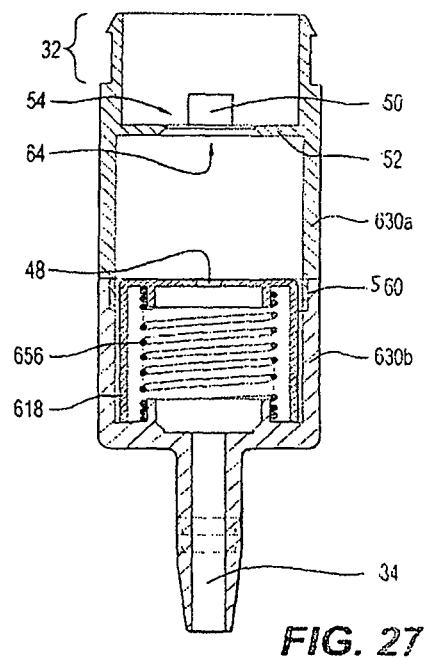
FIG. 27 is a cross-sectional side view of the gas flow indicator apparatus of FIG. 26, taken along and in the direction of arrows 27-27 of FIG. 26.
Figure 28:
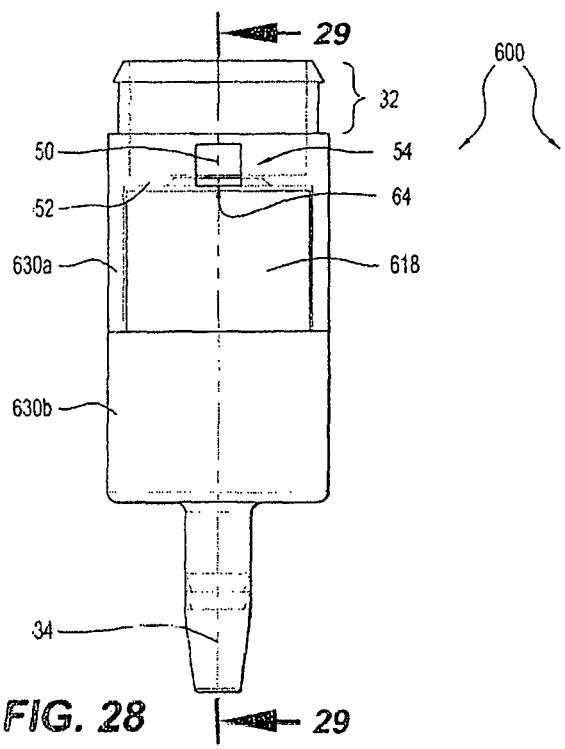
FIG. 28 is a side view of the gas flow indicator apparatus of FIGS. 26 & 27, the apparatus shown in a second state which, in use, indicates that there is gas flow present.
Figure 29:
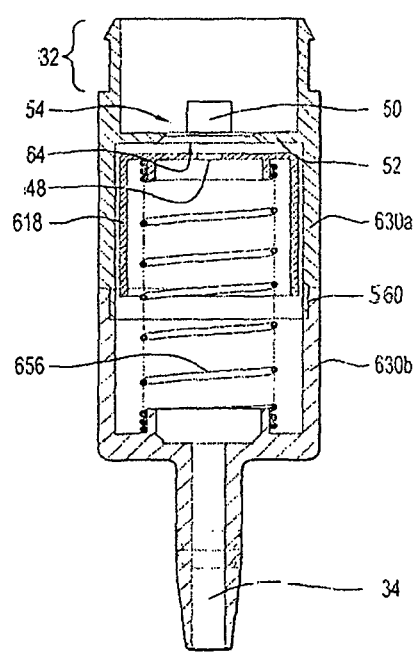
FIG. 29 is a cross-sectional side view of the gas flow indicator apparatus of FIGS. 26 to 28, taken along and in the direction of arrows 29-29 of FIG. 28.

In FIGS. 26 & 27, flow indicator 600 is shown in a first state which, in use, indicates that there is no gas flow present (and/or a desired gas flow rate has not been achieved). Whereas, in FIGS. 28 & 29, flow indicator 600 is shown in a second state which, in use, indicates that there is gas flow present (and/or a minimum gas flow rate has been achieved and/or is being maintained).

Flow indicator 600 operates in substantially the same manner as that of flow indicator 500 of FIGS. 20 to 25, and only varies in respect of the construction and operation of signal means 618 (and its attachment to opaque housing component 630b). That is, in FIGS. 26 to 29, signal means 618 is not a bellows device as in the case of flow indicator 500 of FIGS. 20 to 25, but is instead a piston signal means 618 which moves in and out opaque housing component 630b against/with the action of a suitable biasing means 656, for example, a suitable spring 656 as shown. That is, signal means 618 is biased to its hidden, or partially/substantially hidden, state within opaque housing component 630b, by virtue of spring 656. Further, as signal means 618 is not a bellows device, signal means 618 is not directly connected to opaque housing component 630b, but instead is connected to spring 656, which is in turn connected to opaque housing component 630b. Aside from these constructional differences, flow indicator 600 operates in much the same fashion as that of flow indicator 500, of FIGS. 20 to 25. That is, when gas flow is present (and/or a minimum desired gas flow rate has been achieved and/or maintained) piston signal means 618 travels out of opaque housing component 630b, and into transparent housing, component 630a, and thus into clear sight from the exterior of flow indicator 600. Again, signal means 618 is preferably brightly coloured for ease of visibility in use.

Although not shown in FIGS. 26 to 29, flow indicator 600 could be varied in many ways similar to that previously described with reference to flow indicators 10 to 500. For example, biasing means 656 could be a bellows device instead of a spring. Further, the alignment of piston means 618 could be reversed so that same is disposed in an upright U-shaped configuration, instead of an inverted U-shaped configuration. Further still, vertical ribs, channels, or other protrusions, etc. (none of which are shown in FIGS. 26 to 29), could be provided in order to assist with the movement of piston means 618 and/or to provide a passage for gas flow around piston means 618. These and other variations will be appreciated by a skilled person, and as such, the present invention should not be construed as limited to the specific examples shown and described.

In FIGS. 30 to 33, there is shown a flow indicator 700 made in accordance with still yet a further preferred embodiment of the present invention, flow indicator 700 also being suitable for removable attachment to a gas delivery device or system, such as, for example, the mask 12 of FIGS. 1 & 3, or for permanent attachment thereto during production, assembly or otherwise. It will be appreciated that flow indicator 700 could be designed and provided for attachment to gas delivery devices/systems other than masks (12). Hence, flow indicator 700 of the present invention may be attached to any suitable gas delivery device or system (12), including non-medical gas delivery devices or systems.

Figure 30:
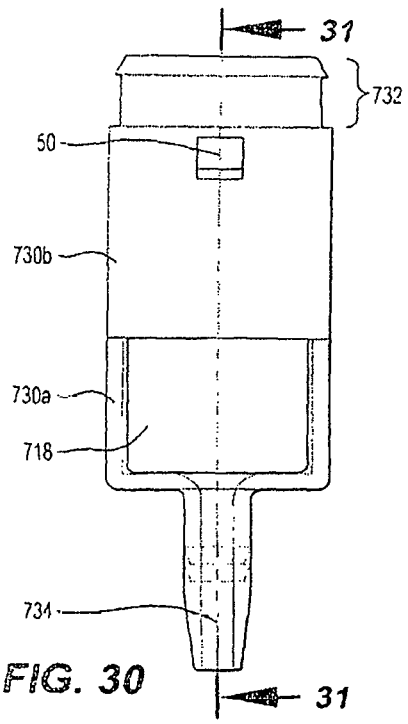
FIG. 30 is a side view of a gas flow indicator apparatus made in accordance with still yet a further preferred embodiment of the present invention, the gas flow indicator apparatus being suitable for removable or permanent attachment to a gas delivery device or system, such as, for example, the mask of FIG. 1, the apparatus shown in a first state which, in use, indicates that there is no gas flow present.
Figure 31:
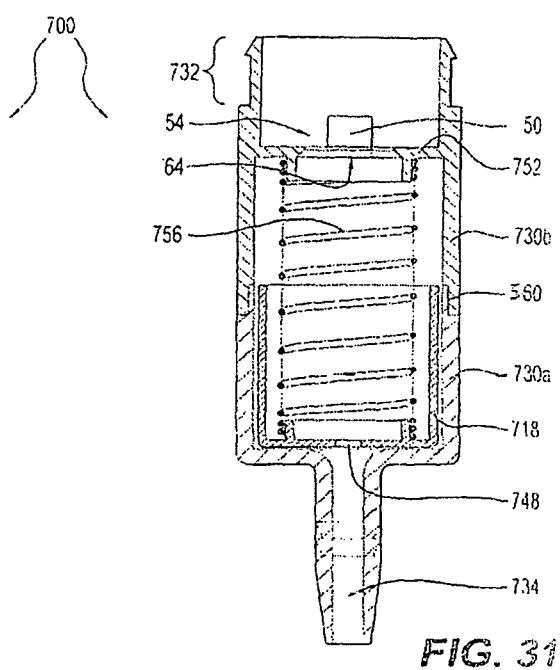
FIG. 31 is a cross-sectional side view of the gas flow indicator apparatus of FIG. 30, taken along and in the direction of arrows 31-31 of FIG. 30.
Figure 32:
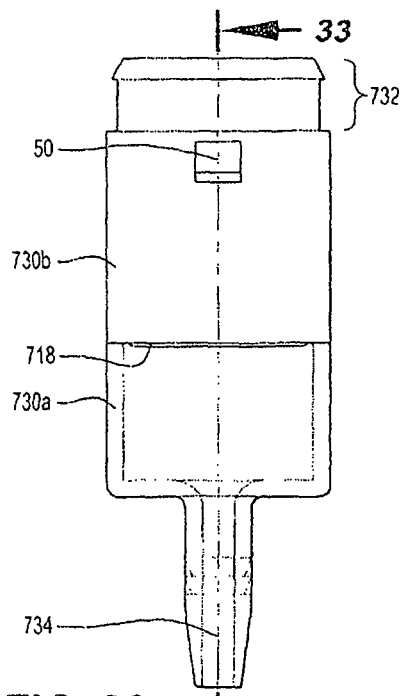
FIG. 32 is a side view of the gas flow indicator apparatus of FIGS. 30 & 31, the apparatus shown in a second state which, in use, indicates that there is gas flow present.

In FIGS. 30 & 31, flow indicator 700 is shown in a first state which, in use, indicates that there is no gas flow present (and/or a desired gas flow rate has not been achieved). Whereas, in FIGS. 32 & 33, flow indicator 700 is shown in a second state which, in use, indicates that there is gas flow present (and/or a minimum gas flow rate has been achieved and/or is being maintained).

Flow indicator 700 is designed to operate in a different, or reverse, manner to that of, for example, flow indicator 600 of FIGS. 26 to 29. That is, signal means 718 is designed to be disposed within transparent housing component 730a when no gas flow is present. Hence, preferred piston signal means 718 of flow indicator 700 is biased to its expanded position relative to the gas supply end of flow indicator 700, by way of, for example, spring 756. In this alternative preferred embodiment, opaque housing component 730b is disposed at the gas delivery device end of flow indicator 700, such that gas flowing into flow indicator 700 acts upon piston signal means 718, and hence forces piston signal means 718 into (or at least substantially into) opaque housing component 730b, and thus, indicates that gas is flowing (and/or a predetermined gas flow rate has been achieved and/or is being maintained).

Figure 33:
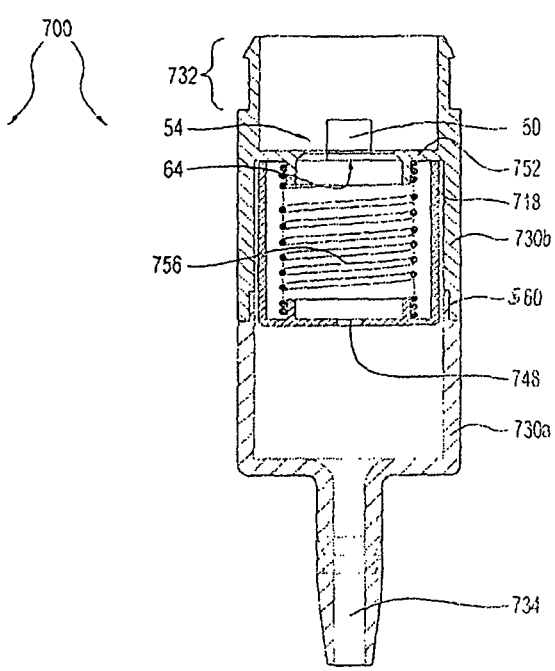
FIG. 33 is a cross-sectional side view of the gas flow indicator apparatus of FIGS. 30 to 32, taken along and in the direction of arrows 33-33 of FIG. 32.

As can be seen in FIGS. 31 & 33, signal means 718 is affixed to annulus 752 by way of spring 756. Supply gas acting on signal means 718 during use of flow indicator 700 may pass through and/or around the piston device (718), but preferably, at least substantially, passes through signal means hole(s) 748.

Although not readily apparent in the drawings provided, piston signal means 718 of flow indicator 700 (or any other suitable signal means 718—not shown) may be dark coloured, and transparent housing component 730a may be fluorescently tinted such that when gas flow is present, and hence when the dark coloured piston signal means 718 moves into, or substantially into, opaque housing component 730b (and out of, or at least substantially out of, transparent housing component 730a), light shining into the fluorescently tinted transparent housing component 730a would clearly indicate that gas flow is present (and/or a predetermined gas flow rate has been achieved). Of course many other such variations are also possible, and hence same should be construed as being included within the scope of the invention as herein described.

Although not shown in FIGS. 30 to 33, flow indicator 700 could be varied in many ways similar to that previously described with reference to flow indicators 10 to 600. For example, biasing means 756 could be a bellows device instead of a spring. Further, the alignment of piston means 718 could be reversed so that same is disposed in an inverted U-shaped configuration, instead of an upright U-shaped configuration. Further still, vertical ribs, channels, or other protrusions, etc. (none of which are shown in FIGS. 30 to 33), could be provided in order to assist with the movement of piston means 718 and/or to provide a passage for gas flow around piston means 718. These and other variations will be appreciated by a skilled person, and as such, the present invention should not be construed as limited to the specific examples shown and described.

In FIGS. 34 & 35, there is shown a flow indicator 800 made in accordance with still yet a further preferred embodiment of the present invention, flow indicator 800 also being suitable for removable attachment to a gas delivery device or system, such as, for example, the mask 12 of FIGS. 1 & 3; or a manual resuscitator device (not shown), e.g. a bag valve mask or "BVM", or for permanent attachment thereto during production, assembly or otherwise. Flow indicator 800 may also be disposed in-line with supply conduit (16), such as, for example, by frictional or permanent splicing. Alternatively, flow indicator 800 may be supplied at any suitable length such that same replaces or becomes the supply conduit (16)—having flow indicator 800 combined therewith. Further, it will be appreciated that flow indicator 800 could be designed and provided for attachment to gas delivery devices/systems other than masks (12), BVMs (12), or supply conduits (16). Accordingly, flow indicator 800 of the present invention may be attached to any suitable gas delivery device, system and/or supply conduit, including non-medical gas delivery devices, systems and/or supply conduits.

Flow indicator 800 operates in substantially the same manner as that of flow indicator 200 of FIGS. 10 & 11, and only varies in respect of the construction of housing 830. That is, like in the case of flow indicators 500,600,700, of FIGS. 20 to 33, housing 830 of flow indicator 800 comprises a transparent housing component 830a, and an opaque housing component 830b. Hence, flow indicator 800 does not require a separate opaque concealment chamber. It will be appreciated that although not shown in FIGS. 34 & 35, flow indicator 800 could be varied in many ways similar to that previously described with reference to flow indicators 10 to 700. For example, bellows means 818 could be replaced with a piston means which is biased to its desired rest position by a spring or a bellows means (856). Should flow indicator 800 include a piston means (818) instead of a bellows means 818, the desired biasing means (856—spring or bellows means, etc.) could be disposed at either of spigots 832 or 834. If biasing means (856) were to be disposed adjacent spigot 832, same would preferably be constructed of a dull or dark coloured material so as to contrast against a preferred bright coloured signal means 818. Further, the alignment of a piston signal means (818) could be reversed so that same is disposed in an upright U-shaped configuration, instead of an inverted U-shaped configuration—for example, referring to FIGS. 30 to 33, if the arrangement of opaque portion 730b and transparent portion 730a were to be reversed, and spring 756 replaced with a bellows biasing means, such an alternative embodiment of flow indicator 800 could be readily provided (in either a mask engaging embodiment or an in-line embodiment). Further still, vertical ribs, channels, or other protrusions, etc. (none of which are shown in FIGS. 34 & 35), could be provided in order to assist with the movement of signal means 818 and/or to provide a passage for gas flow around signal means 818. These and other variations will be appreciated by a skilled person, and as such, the present invention should not be construed as limited to the specific examples shown and described.

While this invention has been described in connection with specific embodiments thereof, it will be understood that it is capable of further modification(s). The present invention is intended to cover any variations, uses or adaptations of the invention following in general, the principles of the invention and including such departures from the present disclosure as come within known or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the attached claims. Various modifications and equivalent arrangements are intended to be included within the spirit and scope of the invention. Therefore, the specific embodiments are to be understood to be illustrative of the many ways in which the principles of the present invention may be practiced.

Where the terms "comprise", "comprises", "comprised" or "comprising" are used in this specification, they are to be interpreted as specifying the presence of the stated features, integers, steps or components referred to, but not to preclude the presence or addition of one or more other features, integers, steps, components to be grouped therewith.

The invention claimed is:
1. A gas flow indicator apparatus comprising:
a housing having first and second adjacent portions that together define a gas flow chamber extending between first and second opposite ends of the housing;

an inlet port at the first of the opposite ends and an outlet port at the second of the opposite ends;

the first portion of the housing is nearer to the inlet port and (i) is an opaque portion or (ii) contains a concealment member, and the second portion is nearer to the outlet port and is transparent; and a gas flow signal device comprising a bellows device that is disposed within the gas flow chamber and is movable in response to gas flow through the gas flow chamber away from the inlet port towards the outlet port;

wherein:
the gas flow signal device is located within the first portion or within the concealment member whereby the bellows device is concealed by the opaque portion or by the concealment member with:
no gas flow through the gas flow chamber, or
gas flow through the gas flow chamber at less than a predetermined gas flow rate; and
the bellows device is movable by being extended, in response to gas flow through the bellows device that comprises:
a gas flow achieving, and/or
a gas flow maintaining,
the predetermined gas flow rate whereby part of the bellows device is disposed within and visible through the transparent second portion to make the predetermined flow rate of gas visually apparent.

2. The gas flow indicator apparatus according to claim 1, further including at least one ambient air inlet hole for entrainment of ambient air during use of the gas flow indicator apparatus.

3. The gas flow indicator apparatus according to claim 1, wherein the predetermined gas flow rate is 6 liters per minute.

4. A gas flow indicator apparatus comprising:
a housing having first and second adjacent portions that together define a gas flow chamber extending between first and second opposite ends of the housing;
an inlet port at the first of the opposite ends and an outlet port at the second of the opposite ends;
the first portion of the housing is nearer to the inlet port and (i) is an opaque portion or (ii) contains a concealment member, and the second portion is nearer to the outlet port and is transparent; and
a gas flow signal device disposed within the gas flow chamber and is movable against a bias, away from the inlet port towards the outlet port, in response to gas flow through the gas flow chamber;

wherein:
the gas flow signal device has an opening whereby a flow of gas from the inlet port to the outlet port is able to pass through the gas flow signal device;
the gas flow signal device is biased to a position within the first portion of the housing or within the concealment member whereby the gas flow signal device is concealed by the first portion or by the concealment member with:
no gas flow through the gas flow chamber, or
gas flow through the gas flow chamber at less than a predetermined gas flow rate; and
the gas flow signal device is movable against the bias, in response to gas flow through the gas flow signal device comprising:
a gas flow achieving, and/or
a gas flow maintaining,
the predetermined gas flow rate whereby part of the gas flow signal device is disposed within and visible through the transparent second portion to make the predetermined flow rate of gas visually apparent.

5. The gas flow indicator apparatus according to claim 4, wherein the opening is at an end of the gas flow signal device remote from the inlet port and the gas flow signal device is movable away from the inlet port towards the outlet port, in response to gas flow through the gas flow chamber, against a bias of a spring that is within the gas flow signal device and acts between the first of the opposite ends of the housing and the end wall of the gas flow signal device.

6. The gas flow indicator apparatus according to claim 4, wherein the opening of the gas flow signal device is at an end of the gas flow signal device remote from the inlet port and the gas flow signal device is movable away from the inlet port towards the outlet port, in response to gas flow through the gas flow chamber, against a bias of a spring that is external to the gas flow signal device and acts between the gas flow signal device and the second of the opposite ends of the housing.

7. The gas flow indicator apparatus according to claim 4, wherein with a gas flow though the gas flow chamber from the inlet port to the outlet port the gas flow signal device enables gas flow between the housing and the gas flow signal device as well as through the gas flow signal device.

8. The gas flow indicator apparatus according to claim 4, further including at least one ambient air inlet hole for entrainment of ambient air during use of the gas flow indicator apparatus.

9. The gas flow indicator apparatus according to claim 4, wherein the predetermined gas flow rate is 6 liters per minute.

10. A gas flow indicator apparatus comprising:
a housing having first and second adjacent portions that together define a gas flow chamber extending between first and second opposite ends of the housing;
an inlet port at the first of the opposite ends and an outlet port at the second of the opposite ends;
the first portion of the housing is nearer to the inlet port and is transparent, and the second portion is nearer to the outlet port and (i) is an opaque portion or (ii) contains a concealment member; and
a gas flow signal device disposed within the gas flow chamber and is movable against a bias, away from the inlet port towards the outlet port, in response to gas flow through the gas flow chamber;

wherein:
the gas flow signal device has an opening whereby a flow of gas from the inlet port to the outlet port is able to pass through the gas flow signal device;
the gas flow signal device is biased to a position within the first portion of the housing whereby the gas flow signal device is disposed within and visible through the transparent first portion to make visually apparent the presence of:
no gas flow through the gas flow chamber, or
gas flow through the gas flow chamber at less than a predetermined gas flow rate; and
the gas flow signal device is movable against the bias, in response to gas flow through the cylinder device comprising:
a gas flow achieving, and/or
a gas flow maintaining,
the predetermined gas flow rate whereby the gas flow signal device is disposed within and concealed by the second portion of the housing or within the concealment member to make the predetermined flow rate of gas visually apparent.

11. The gas flow indicator apparatus according to claim 10, wherein the opening of the gas flow signal device is at an end of the gas flow signal device proximate to the inlet port and the gas flow signal device is movable away from the inlet port towards the outlet port, in response to gas flow through the gas flow chamber, against a bias of a spring that is within the gas flow signal device and acts between the second of opposite ends of the housing and the gas flow signal device.

12. The gas flow indicator apparatus according to claim 10, wherein with a gas flow though the gas flow chamber from the inlet port to the outlet port the gas flow signal device enables gas flow between the housing and the gas flow signal device as well as through the opening of the gas flow signal device.

13. The gas flow indicator apparatus according to claim 10, further including at least one ambient air inlet hole for entrainment of ambient air during use of the gas flow indicator apparatus.

14. The gas flow indicator apparatus according to claim 10, wherein the predetermined gas flow rate is 6 liters per minute.

* * * * *